United States Patent [19]

Ahmed et al.

[11] Patent Number: 5,922,653
[45] Date of Patent: Jul. 13, 1999

[54] COMPOSITIONS AND PROCESSES FOR TREATING SUBTERRANEAN FORMATIONS

[75] Inventors: Iqbal Ahmed; Ahmad Moradi-Araghi; Bharat B. Patel; Wayne S. Stewart, all of Bartlesville, Okla.

[73] Assignee: Phillips Petroleum Company, Bartlesville, Okla.

[21] Appl. No.: 08/723,635

[22] Filed: Oct. 3, 1996

Related U.S. Application Data

[63] Continuation-in-part of application No. 08/575,429, Dec. 20, 1995, Pat. No. 5,708,107.

[51] Int. Cl.$^6$ .............................. C09K 3/00; C09K 7/00; E21B 43/17; C08F 26/08
[52] U.S. Cl. ...................... 507/242; 526/263; 526/277; 526/287; 526/310; 526/291; 507/130; 166/308
[58] Field of Search .................... 526/263, 277, 526/287, 310, 291; 507/242

[56] References Cited

U.S. PATENT DOCUMENTS

| | | | |
|---|---|---|---|
| 4,317,487 | 3/1982 | Merkl | 166/305 |
| 4,454,114 | 6/1984 | Strasilla et al. | 424/70 |
| 4,460,570 | 7/1984 | Strasilla et al. | 424/70 |
| 4,507,440 | 3/1985 | Engelhardt et al. | 507/242 |
| 4,609,476 | 9/1986 | Heilweil | 507/242 |
| 4,661,266 | 4/1987 | Kanda et al. | 507/242 |
| 4,848,570 | 7/1989 | Korpics | 166/312 |
| 4,928,766 | 5/1990 | Hoskin | 166/270 |
| 5,003,016 | 3/1991 | Boeder | 526/208 |
| 5,028,344 | 7/1991 | Hoskin | 252/8.554 |
| 5,129,457 | 7/1992 | Sydansk | 166/274 |
| 5,270,382 | 12/1993 | Ahmed et al. | 524/809 |
| 5,294,691 | 3/1994 | Ahmed et al. | 526/287 |
| 5,391,669 | 2/1995 | Sulc et al. | 526/265 |
| 5,650,633 | 7/1997 | Ahmed et al. | 252/183.11 |

FOREIGN PATENT DOCUMENTS

| | | |
|---|---|---|
| 5-179155 | 12/1991 | Japan . |
| 7-258202 | 3/1994 | Japan . |
| 7-300513 | 5/1994 | Japan . |

OTHER PUBLICATIONS

Macromolecules, 1994, 27, 2165–2173.

*Primary Examiner*—C. H. Kelly
*Attorney, Agent, or Firm*—Lucas K. Shay

[57] ABSTRACT

A composition and a process for using the composition for applications in a subterranean formation are provided. The composition comprises a clay, a polymer, and a liquid. The polymer comprises repeat units derived from a nitrogen-containing olefinic monomer and optionally an olefinic comonomer. The composition can be used as or in drilling fluids, workover fluids, completion fluids, or combinations of any two or more thereof.

53 Claims, No Drawings

COMPOSITIONS AND PROCESSES FOR TREATING SUBTERRANEAN FORMATIONS

This application is a continuation-in-part of application Ser. No. 08/575,429, filed Dec. 20, 1995, U.S. Pat. No. 5,708,107.

FIELD OF THE INVENTION

The present invention relates to compositions which can be used to prepare water-soluble polymers that are useful in oil field applications and processes for producing the compositions; to water-soluble polymers which can be prepared from the compositions and nitrogen-containing olefinic compounds as well as processes for producing and using the water-soluble polymers; and to gelling compositions produced from the water-soluble polymers for applications in a subterranean formation such as, for example, altering permeability correcting water coning problems and processes for producing and using the gelling compositions.

BACKGROUND OF THE INVENTION

It is well known to those skilled in the art that polymers and gelled or crosslinked water-soluble polymers are useful in enhanced oil recovery and other oil field operations. They have been used to alter the permeability of underground formations in order to enhance the effectiveness of water flooding operations. Generally, polymers or polymers along with a gelling agent such as an appropriate crosslinking agent in a liquid are injected into the formation. The polymers then permeate into and gel, in the cases when a polymer and a crosslinking agent are used, in the regions having the highest water permeability.

Polymers have also been used in subterranean formation treatments such as "matrix acidizing" and "fracture acidizing". Because such treatments are well known to one skilled in the art, description of which is omitted herein and can be found in U.S. Pat. No. 4,997,582, description of which is herein incorporated by reference.

Because of environmental concerns as well as cost for disposing of a produced brine which is defined as the brine co-produced with oil and gas and is generally contaminated with some oil, or gas, or both, it is desirable to utilize the produced brine as the liquid used for the polymers and appropriate crosslinking systems. Use of produced brines eliminates not only the cost associated with acquiring and pre-treating fresh water for use as the liquid but also the disposal cost for the produced brine. Most produced brines are known to be hard brines, i.e., those having a divalent cation concentration greater than 1000 ppm.

Many polymers have been developed and used in processes for the recovery of hydrocarbons. Generally a desirable property is that such polymers impart to a liquid an increased viscosity when a relatively small quantity of the polymer is added, and preferably at a minimal cost. Another desirable property is that such polymers form gels, in the presence of a suitable gelling agent such as a crosslinking agent. However, a number of such polymers are not capable of forming gels having high thermal stability, i.e., the gels formed show high syneresis after a short period, such as for example a few days, at high temperature, such as for example, 120° C. in a harsh environment such as sea water.

Various polymers of desired properties such as those disclosed above may be used in the process for recovery of hydrocarbons. For example, multivalent metallic ions crosslink gellable polymers through the interaction with the oxygen atoms of the polymer molecules. Therefore, the gellable polymers generally contain some carboxylate groups. Generally, the gellable polymers used such as, for example, partially hydrolyzed polyacrylamide are of high molecular weight and contain high degrees of hydrolysis, i.e., contain 10–30 mole % carboxylate groups. However, these high molecular weight and/or high mole % carboxylate group-containing polymers gel almost instantly in the presence of the above-described multivalent metallic compounds. Such fast gelation rate renders the application of gelling compositions containing these polymers and multivalent metallic compounds not useful in many oil-field applications such as, for example, water shut-offs and permeability reductions.

Many processes have been developed to delay the gelation of gelling compositions by adding a gelation delaying agent to the gelling compositions. However, a gelation delaying agent is not inexpensive and a gelation delaying agent often adds appreciable costs to oil field operation. Furthermore, many gellable polymers cannot withstand a hostile environment as described above.

There is therefore an increasing demand for water-soluble polymers that can be used to prepare gels which withstand hostile environments. A hostile environment includes, but is not limited to, high temperatures, high salinity and/or high content of divalent metal cations, commonly known as "hardness ions", as well as the high acidity, temperature and shear conditions encountered in processes such as acid fracturing.

In the art of drilling wells to tap subterranean deposits of natural resources, such as gas, geothermal steam or oil, it is well known to use a drilling fluid. In addition to having the desirably rheological properties such as viscosity and gel strength, it is very important that such drilling fluids exhibit a low rate of filtration or water loss, that is, the drilling fluid must prevent excessive amounts of fluid, or "filtrate", flowing from the bore hole into the surrounding formation. The loss of water or other fluid from the drilling hole is prevented by the formation of a filter cake which deposits from the drilling fluid and seals the wall of the bore hole. Numerous formulations, compositions and additives to optimize the performance of drilling fluids for various applications have been developed. For instance, compositions comprising mixtures of carboxylic acid polymers and soluble metal salts with the object of increasing the "yield" (defined as the number of barrels of 15 centipoise mud which can be prepared from one ton of clay) of relatively low-grade clays have been used.

Excessive fluid loss from the drilling fluid may contaminate the producing formation, permanently displacing oil and blocking production. The adverse consequences of excessive fluid loss in the drilling of very deep wells are more severe due to the high temperatures and pressures encountered in such drilling operations. The viscosity of a fluid normally decreases with an increase in temperature, but certain polymer additive or deflocculating agents may reduce, or even reverse, this tendency. However, the polymers which are most effective in achieving this effect are the most vulnerable to breakdown through oxidation, shear and thermal effects, i.e., the duration of exposure to high temperature drilling operations. Also, many such polymers tend to precipitate and/or lose viscosity as well as effectiveness as water loss additives when exposed to dissolved electrolytes, particularly when divalent metal cations such as $Ca^{+2}$ and $Mg^{+2}$ are present. In drilling fluids, the resulting vulnerability to breakdown is exacerbated by the density of drilling mud, which is directly related to weighting agents required for a given formation pressure.

Breakdown of polymers causes a large increase in the fluid loss accompanied by an increase in filter cake thickness. These conditions often result in differential sticking of the drill string. It is, therefore, desirable to develop additives which enable drilling fluids to retain their proper viscosity and fluid content over a broader range of conditions.

Drilling fluids are used in the drilling of various types of wells. Workover and completion fluids, in contrast, are those fluids used in the completion and servicing of such wells. Completion fluids are those fluids used after drilling is complete and during the steps of completion, or recompletion, of the well. Completion can include cementing the casing, perforating the casing, setting the tubing and pump, etc.

Workover fluids are those fluids used during remedial work in the well. This can include removing tubing, replacing a pump, cleaning out sand or other deposits, logging, reperforating, etc. Workover also broadly includes steps used in preparing an existing well for secondary or tertiary oil recovery such as polymer additions, micellar flooding, steam injection, etc.

Both workover and completion fluids are used in part to control well pressure, to prevent the collapse of casing from overpressure, and to prevent or reduce corrosion of casing. A drilling fluid may be suitable for completion or workover over applications in some cases, but not in all cases.

Although there has been considerable progress in the field of Workover and completion fluids, there is significant room for further improvement. For example, wells are being completed and serviced in increasingly hostile environments involving, e.g., high temperatures and high levels of salinity and/or hardness in the formation water. Thus, new additives for Workover and completion fluids which retain their properties at elevated temperatures and high concentrations of dissolved electrolytes are in demand.

Therefore, a composition which can be used to prepare a more hostile environment-withstanding polymer as well as a hostile environment-withstanding gelling composition, containing the hostile environment-withstanding polymer, that can form stable gels in a liquid such as, for example, produced brines, for near-wellbore as well as in-depth treatments, and preferably that does not require a gelation delaying agent, is highly desirable. It is also highly desirable to develop a composition which can be used in drilling fluids, completion fluids, or Workover fluids.

SUMMARY OF THE INVENTION

An object of the invention is to provide a composition which can be used as a monomer to synthesize a hostile environment-withstanding, water-soluble polymer. Another object of the invention is to provide a process for synthesizing the composition. Yet another object of the present invention is to provide a water-soluble polymer that can be used to form a gel in a hostile environment in hydrocarbon-bearing subterranean formations. Also an object of the invention is to provide a process for altering the permeability of hydrocarbon-bearing subterranean formations using the water-soluble polymer or for other drilling applications. A further object of the invention is to provide a gelling composition which contains the water-soluble polymer and withstands a hostile environment. Still another object of the present invention is to provide a process for various drilling applications or for altering the permeability of hydrocarbon-bearing subterranean formations by using a gelling composition that contains the water-soluble polymer, withstands hostile environment, and is environmentally suitable for use in subterranean formations. Still a further object of the invention is to provide a process for various drilling applications or for altering the permeability of hydrocarbon-bearing subterranean formations with a gelling composition that does not require a gelation delaying agent. Yet still another object of the invention is to provide a process for treatment of subterranean formations employing a gelling composition that is environmentally suitable for subterranean formation operations. An advantage of the invention is that the gelling compositions of the invention generally withstand a hostile environment and the processes generally do not employ a gelation delaying agent, yet achieve the alteration of permeability of the formations or can be used in other applications. Other objects, features, and advantages will become more apparent as the invention is more fully disclosed hereinbelow.

According to a first embodiment of the present invention, a composition that can be used to prepare a water-soluble polymer which can be used in a hydrocarbon-bearing subterranean formation is provided. The composition comprises a nitrogen-containing olefinic compound.

According to a second embodiment of the present invention, a process for preparing a composition is provided that can be used to prepare a water-soluble polymer which can be used in a hydrocarbon-bearing formation wherein said composition comprises a nitrogen-containing olefinic compound.

According to a third embodiment of the present invention, a water-soluble polymer which can be used in a hydrocarbon-bearing formation is provided. The polymer comprises repeat units derived from at least one nitrogen-containing olefinic compound.

According to a fourth embodiment of the present invention, a process which can be used for treating hydrocarbon-bearing formation is provided comprises introducing into the formation a water-soluble composition wherein the water-soluble composition comprises a water-soluble polymer comprising repeat units derived from at least one nitrogen-containing olefinic compound.

According to a fifth embodiment of the present invention, a gelling composition is provided which comprises a water-soluble polymer, a crosslinking agent, and a liquid wherein the water-soluble polymer comprises repeat units derived from at least one nitrogen-containing olefinic compound.

According to a sixth embodiment of the present invention, a process is provided which comprises introducing into a subterranean formation a gelling composition comprising a water-soluble polymer, a crosslinking agent, and a liquid wherein the gelling composition forms gels when introduced into the formation and the water-soluble polymer comprises repeat units derived from at least one nitrogen-containing olefinic compound.

According to a seventh embodiment of the present invention a composition which can be used as or in drilling fluid, completion fluid, workover fluid, or combinations of any two or more thereof is provided. The composition can comprise, consist essentially of, or consist of a water-soluble polymer, a clay, and a liquid wherein the polymer comprises repeat units derived from at least one nitrogen-containing olefinic compound.

DETAILED DESCRIPTION OF THE INVENTION

According to the first embodiment of the present invention, a composition useful as a monomer for synthesizing a water-soluble polymer is provided. The composition comprises, or consists essentially of, or consists of a nitrogen-containing olefinic compound having the formula selected from the group consisting of sulfobetaines, vinylic amides, and combinations of any two or more thereof wherein the sulfobetaine has the formula of $R_1C(R_1)\!=\!C(R_1)\!-\!(C\!=\!O)_m\!-\!(Ar)_m\!-\!Y\!-\!N^+(R_2)(R_2)\!-\!Y\!-\!SO_3^-$ the vinylic amide has the formula of phosphonates, sulfinates, phosphinates, and combinations of any two or more thereof. Each m can be the same or different and is 0 or 1.

Examples of suitable nitrogen-containing olefinic compounds of the first embodiment of the invention include, but are not limited to, N,N-dimethyl-N-(3-sulfopropyl)-N-(4-vinylbenzyl) ammonium inner salt, N,N-dimethyl-N-(3-sulfobutyl)-N-(4-vinylbenzyl) ammonium inner salt, N,N-diethyl-N-(3-sulfopropyl)-N-(4-vinylbenzyl) ammonium inner salt, N,N-diethyl-N-(3-sulfobutyl)-N-(4-vinylbenzyl) ammonium inner salt, N,N-dimethyl-N-(3-sulfopropyl)-N-(3-vinylbenzyl) ammonium inner salt, N,N-dimethyl-N-(3-sulfobutyl)-N-(3-vinylbenzyl) ammonium inner salt, N,N-diethyl-N-(3-sulfopropyl)-N-(3-vinyl benzyl) ammonium inner salt, N,N-diethyl-N-(3-sulfobutyl)-N-(3-vinylbenzyl) ammonium inner salt, N-acryloyl-N'-methyl-N'-(2-amino-2-oxoethyl) piperazinium chloride, N-acryloyl-N'-methyl-N'-(3-amino-3-oxopropyl) piperazinium chloride, N-acryloyl-N'-methyl-N'-(4-amino-4-oxobutyl) piperazinium chloride, N-acryloyl-N'-ethyl-N'-(2-amino-2-oxoethyl) piperazinium chloride, N-acryloyl-N'-ethyl-N'-(3-amino-3-oxopropyl) piperazinium chloride, N-acryloyl-N'-ethyl-N'-(4-amino-4-oxobutyl) piperazinium chloride, N,N-dimethyl-N-(2-amino-2-oxoethyl)-N-(4-vinylbenzyl) ammonium chloride, N,N-diethyl-N-(2-amino-2-oxoethyl)-N-(4-vinylbenzyl) ammonium chloride, N,N-dimethyl-N-(3-amino-3-oxopropyl)-N-(4-vinylbenzyl) ammonium chloride, N,N-diethyl-N-(3-amino-3-oxopropyl)-N-(4-vinylbenzyl) ammonium chloride, N-(2-amino-2-oxoethyl)-N'-vinylimidazolium chloride, N-(3-amino-3-oxopropyl)-N'-

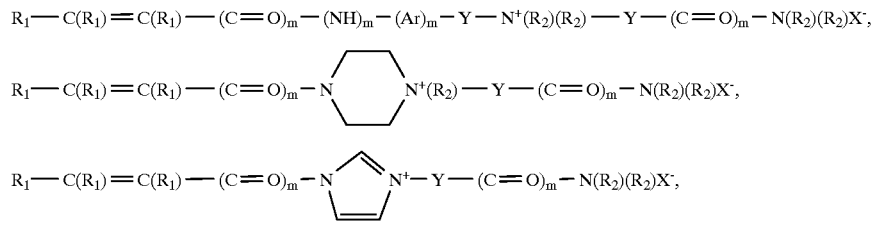

or combinations of any two or more thereof. $R_1$ and $R_2$ can be the same or different and are each independently selected from the group consisting of hydrogen, alkyl radicals, aryl radicals, aralkyl radicals, alkaryl radicals, and combinations of any two or more thereof wherein each radical can contain 1 to about 30, preferably 1 to abut 20, more preferably 1 to about 15, and most preferably 1 to 10 carbon atoms and can contain functional group(s) such as ammonium, hydroxyl, sulfate, ether, carbonyl groups, amine groups, sulfhydryl groups, or combinations of any two or more thereof which can contribute to water solubility of polymers produced therefrom. Preferably $R_1$ is hydrogen and $R_2$ is hydrogen, methyl, ethyl, or combinations of two or more thereof. Y is an alkylene radical, a phenylene group, an imidazolium group, a naphthylene group, a biphenylene group, or combinations of any two or more thereof. Each Y is preferably independently an alkylene radical which can have 1 to about 20, preferably 1 to about 15, and more preferably 1 to 10 carbon atoms. Most preferably, Y is a short alkylene radical having 1 to about 5 carbon atoms. Ar is an arylene radical, preferably a phenyl group, which can be substituted or unsubstituted. X is an anion selected from the group consisting of halides, sulfates, phosphates, nitrates, sulfonates, vinylimidazolium chloride, N-(4-amino-4-oxobutyl)-N'-vinylimidazolium chloride, and combinations of any two or more thereof.

The nitrogen-containing olefinic compounds of the first embodiment of the invention can be prepared by the process disclosed hereinbelow in the second embodiment of the invention.

In the second embodiment of the present invention, a process for preparing the nitrogen-containing olefinic compounds is provided. The nitrogen-containing olefinic compounds having the formula of $R_1C(R_1)\!=\!C(R_1)\!-\!(C\!=\!O)_m\!-\!(NH)_m\!-\!(Ar)_m\!-\!Y\!-\!N^+(R_2)(R_2)\!-\!Y\!-\!SO_3^-$ (a sulfobetaine), can be produced by contacting a vinylic tertiary amine with an alkylating agent such as, for example, an alkylsulfonic acid containing a proper leaving group such as halide, hydroxyl, tosylate, other suitable leaving groups, or combinations of any two or more thereof. These reagents can be contacted, under any suitable conditions so long as the conditions can effect the production of the nitrogen-containing olefinic compounds, in a solvent such as toluene, benzene, pentane, hexane, acetonitrile, methanol, ethanol, any other common organic solvent or combinations of any two or more solvents. Generally, a tertiary amine can be contacted with an alkylating agent at a temperature in the range of from about 10 to about 120° C., preferably about 20 to about 90° C., and most preferably 35 to 65° C. for about 1 to about 10 days, preferably about 1 to about 8 days, and most preferably 1 to 5 days under any suitable pressures such as, for example, about 1 atmospheric pressure. A suitable radical inhibitor such as 1,3-dinitrobenzene can be added to prevent polymerization of the nitrogen-containing olefinic compounds during the contacting. Preferably the production is carried out by using 1,3-propanesultone or 1,4-butanesultone as the alkylating reagent in toluene by heating at 45–50° C. for 72 hours. The sulfobetaine generally precipitates from the solvent and can be purified by filtration, repeated washing with any common organic solvent that does not dissolve the sulfobetaine, and finally dried under reduced pressure. Preferably diethyl ether is used to wash the sulfobetaine during filtration, and the product can be dried under a pressure such as, for example, 5 cm Hg for 48 hours.

Examples of suitable tertiary amines include, but are not limited to, N,N-dimethyl-N-(4-vinylbenzyl) amine, N,N-dimethyl-N-(4-vinylbenzyl) amine, N,N-diethyl-N-(4-vinylbenzyl) amine, N,N-diethyl-N-(4-vinylbenzyl) amine, N,N-dimethyl-N-(3-vinylbenzyl) amine, N,N-dimethyl-N-(3-vinylbenzyl) amine, N,N-diethyl-N-(3-vinylbenzyl) amine and N,N-diethyl-N-(3-vinylbenzyl) amine, and combinations of any two or more thereof.

Examples of suitable alkylating reagents include, but are not limited to, 3-chloro-propane-1-sulfonic acid, 4-chloro-butane-1-sulfonic acid, 3-hydroxy-propane-1-sulfonic acid, 4-hydroxy-butane-1-sulfonic acid, the corresponding esters of the hydroxy-alkane-1-sulfonic acids such as 1,3-propanesultone and 1,4-butanesultone, and combinations of any two or more thereof.

The nitrogen-containing olefinic compounds with the amide functional group of the first embodiment of the invention have general formulae of lating agent can be contacted under a condition including a temperature in the range of from about 10 to about 150° C., preferably about 20 to about 120° C., and most preferably 30 to 100° C. for about 1 to about 15 days, preferably 1 to 8 days under any suitable pressure such as, for example, about 1 atmospheric pressure. A suitable radical inhibitor such as, for example, 1,3-dinitrobenzene can be added to prevent polymerization of the nitrogen-containing olefinic compounds during the contacting. Preferably the production is carried out by using 2-chloro-acetamide as the alkylating agent in acetonitrile by heating at 45–80° C. for 50–150 hours. The nitrogen-containing olefinic compounds generally precipitate from the solvent and can be purified by filtration, repeated washing with any common organic solvent that does not dissolve the nitrogen-containing olefinic compounds, and finally dried under reduced pressure. Preferably diethyl ether is used to wash the nitrogen-containing olefinic compounds during filtration, and the nitrogen-containing olefinic compounds generally can be dried under a suitable pressure such as, for example, 5 cm Hg for 48 hours.

Examples of suitable vinyl-substituted amines include, but are not limited to, N,N-dimethyl-N-(4-vinylbenzyl) amine, N,N-dimethyl-N-(4-vinylbenzyl) amine, N,N-diethyl-N-(4-vinylbenzyl) amine, N,N-diethyl-N-(4-vinylbenzyl) amine, N,N-dimethyl-N-(3-vinylbenzyl) amine, N,N-dimethyl-N-(3-vinylbenzyl) amine, N,N-diethyl-N-(3-vinylbenzyl) amine and N,N-diethyl-N-(3-vinylbenzyl) amine, and combinations of any two or more thereof.

Examples of suitable alkylating agents include, but are not limited to, 2-chloro-acetamide, 2-bromo-acetamide, 3-chloro-propaneamide and 3-bromo-propaneamide, and combinations of any two or more thereof.

In the second embodiment of the invention, the molar ratio of the alkylating agent to the amine can be any ratio so long the ratio can effect the production of the nitrogen-containing olefinic compounds. Generally, the molar ratio can be in the range of from about 1:0.01 to about 0.01: 1, preferably about 1:0.05 to about 0.05:1, and most preferably 1:0.1 to 0.1:1. The molar ratio of the radical inhibitor to the

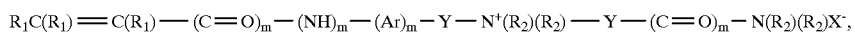

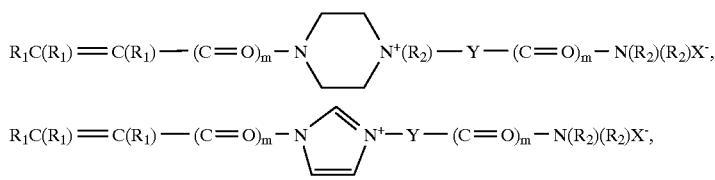

and combinations of any two or more thereof. These compounds can be produced by alkylation of a vinyl-substituted amine with an alkylating agent such as, for example, an alkyl amide containing a proper leaving group such as halide, hydroxyl, tosylate, other suitable leaving groups, or combinations of any two or more thereof. These reagents can be contacted, under any conditions so long as the conditions can effect the production of the nitrogen-containing olefinic compounds in a solvent such as toluene, benzene, pentane, hexane, acetonitrile, methanol, ethanol, any other common organic solvents, or combinations of any two or more thereof. Generally, a vinyl-substituted amine and an alkyamine can be in the range of from about 0.1:1 to about 1,000:1. The molar ratio of the solvent to the amine can be any ratio that is effective in the production of a nitrogen-containing olefinic compound and can be in the range of from about 0.1:1 to about 1,000:1.

According to the third embodiment of the present invention, a water-soluble polymer is provided which can withstand a hostile environment and can be used for treating a hydrocarbon-bearing subterranean formation. The water-soluble polymer comprises, or consists essentially of, or consists of, repeat units derived from at least one nitrogen-containing olefinic compound. The term "polymer" as used herein denotes a molecule having at least about 10 repeat units and can be homopolymer, copolymer, terpolymer, tetrapolymer, or combination of any two or more thereof.

Any nitrogen-containing olefinic compounds having a polymerizable ethylenic linkage and being capable of producing a polymer which withstands hostile environment can be used for preparing the water-soluble polymer of the third embodiment of the present invention. Though it is not necessary, it is preferred that the ethylenic linkage be at the terminal end of the nitrogen-containing olefin molecule and that at least one nitrogen be a tertiary amine. The presently preferred repeat units include, but are not limited to of $R_1$—$C(R_1)$=$C(R_1)$—W, $R_1$—$C(R_1)$=$C(R_1)$—(C=O)$_m$—Z, $R_1$—$C(R_1)$=$C(R_1)$—Y—W, $R_1$—$C(R_1)$=$C(R_1)$—(C=O)$_m$—N($R_2$)—Y—$R_2$, $R_1$—$C(R_1)$=$C(R_1)$—(C=O)$_m$—GY—Z, $R_1C(R_1)$=$C(R_1)$—(C=O)$_m$—G—Y—W, $R_1$—$C(R_1)$=$C(R_1)$—(C=O)$_m$—Y—Z, and combinations of any two or more thereof wherein Z has a formula selected from the group consisting of $N(R_2)(R_2)$, $N^+(R_2)(R_2)(R_2)X^-$, and combinations of any two or more thereof wherein X is an anion selected from the group consisting of halides, sulfate, phosphate, nitrate, sulfonates, phosphonates, sulfinates, phosphinates, and combinations of any two or more thereof. M, Y, $R_1$, and $R_2$ are the same as those disclosed above. The letter m is 0 or 1. G is $N(R_1)$ or O. W

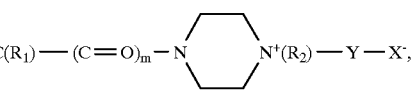

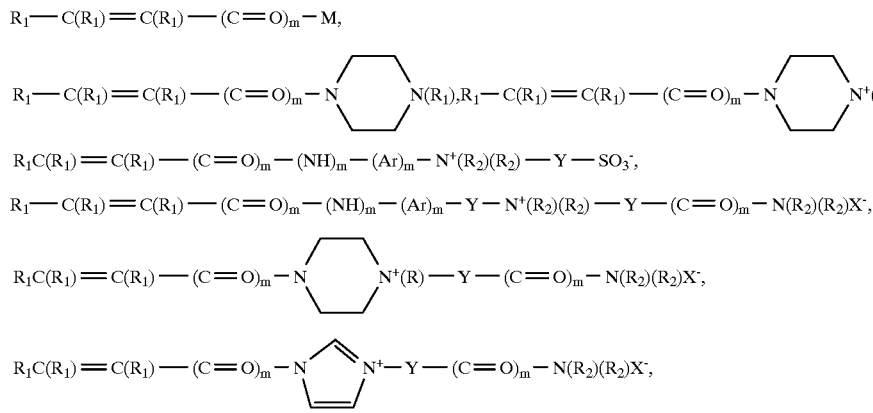

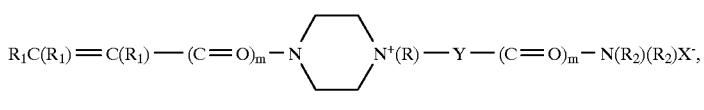

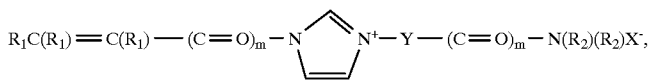

and combinations of any two or more thereof. $R_1$ and $R_2$ can be the same or different and are each independently selected from the group consisting of hydrogen, alkyl radicals, aryl radicals, aralkyl radicals, alkaryl radicals, and combinations of any two or more thereof wherein each radical can contain 1 to about 30, preferably 1 to abut 20, more preferably 1 to about 15, and most preferably 1 to 10 carbon atoms and can contain functionalities such as, for example, hydroxyl, sulfate, carbonyl, amine, sulfhydryl, or combinations of any two or more thereof. Preferably $R_1$ is hydrogen, $R_2$ is hydrogen, methyl, ethyl, or combinations of any two or more thereof. M is a morpholine group which can be substituted or unsubstituted. Y is an alkylene radical, a phenyl group, an imidazolium group, a naphthyl group, a biphenyl group, or combinations of any two or more thereof which can have 1 to about 20, preferably 1 to about 15, and most preferably 1 to 10 carbon atoms. Most preferably, Y is a short alkylene radical having 1 to about 5 carbon atoms. Ar is an arylene radical, preferably phenyl, which can be substituted or unsubstituted. X is an anion selected from the group consisting of halides, sulfate, phosphate, nitrate, sulfonates, phosphonates, sulfinates, phosphinates, and combinations of any two or more thereof. Each m can be the same or different and is independently 0 or 1.

The water-soluble polymer of the third embodiment of the present invention can be a homopolymer, copolymer, terpolymer or tetrapolymer. However, if the nitrogen-containing olefinic repeat units contain an amide group, it is preferred that the water-soluble polymer be derived from repeat units comprising at least one of the nitrogen-containing olefinic compounds described above and at least one olefinic comonomer selected from the group consisting of is an acid moiety selected from the group consisting of phosphinic acid, phosphonic acid, sulfonic acid, sulfonic acid, sulfuric acid, sulfurous acid, carboxylic acid, phosphoric acid, ammonium salts or alkali metal salts of these acids, and combinations of any two or more thereof.

Examples of suitable nitrogen-containing olefinic compounds of the third embodiment of the invention include, but are not limited to, N-acryloyl morpholine, N-acryloyl-N'-methyl piperazine, N-acryloyl-N'-ethyl piperazine, N-acryloyl-N'-propyl piperazine, N-acryloyl-N'-(3-sulfopropyl)-N'-methyl piperazinium inner salt, N-acryloyl-N'-(3-sulfopropyl)-N'-ethyl piperazinium inner salt, N-acryloyl-N'-(4-sulfopropyl)-N'-methyl piperazinium inner salt, N-acryloyl-N'-(4-sulfopropyl)-N'-ethyl piperazinium inner salt, N-acryloyl-N'-(2-amino-2-oxoethyl)-N'-methyl piperazinium chloride, N-acryloyl-N'-(3-amino-3-oxopropyl)-N'-methyl piperazinium chloride, N-acryloyl-N'-(4-amino-4-oxobutyl)-N'-methyl piperazinium chloride, N-acryloyl-N'-(2-amino-2-oxoethyl)-N'-ethyl piperazinium chloride, N-acryloyl-N'-(3-amino-3-oxopropyl)-N'-ethyl piperazinium chloride, N-acryloyl-N'-(4-amino-4-oxobutyl)-N'-ethyl piperazinium chloride, N,N-dimethyl-N-(3-sulfopropyl)-N-(4-vinylbenzyl) ammonium inner salt, N,N-dimethyl-N-(4-sulfobutyl)-N-(4-vinylbenzyl) ammonium inner salt, N,N-diethyl-N-(3-sulfopropyl)-N-(4-vinylbenzyl) ammonium inner salt, N,N-diethyl-N-(4-sulfobutyl)-N-(4-vinylbenzyl) ammonium inner salt, N,N-dimethyl-N-(3-sulfopropyl)-N-(3-vinylbenzyl) ammonium inner salt, N,N-dimethyl-N-(4-sulfobutyl)-N-(3-vinylbenzyl) ammonium inner salt, N,N-diethyl-N-(3-sulfopropyl)-N-(3-vinylbenzyl) ammonium inner salt, N,N- diethyl-N-(4-sulfobutyl)-N-(3-vinylbenzyl) ammonium inner salt, N,N-dimethyl-N-(2-amino-2-oxoethyl)-N-(4-vinylbenzyl) ammonium chloride, N,N-diethyl-N-(2-amino-2-oxoethyl)-N-(4-vinylbenzyl) ammonium chloride, N,N-dimethyl-N-(3-amino-3-oxopropyl)-N-(4-vinylbenzyl) ammonium chloride, N,N-diethyl-N-(3-amino-3-oxopropyl)-N-(4-vinylbenzyl) ammonium chloride, N,N-dimethyl-N-(2-amino-2-oxoethyl)-N-(3-vinylbenzyl) ammonium chloride, N,N-diethyl-N-(2-amino-2-oxoethyl)-N-(3-vinylbenzyl) ammonium chloride, N,N-dimethyl-N-(3-amino-3-oxopropyl)-N-(3-vinylbenzyl) ammonium chloride, N,N-diethyl-N-(3-amino-3-oxopropyl)-N-(3-vinylbenzyl) ammonium chloride, N-(2-amino-2-oxoethyl)-N'-vinyl imidazolium chloride, N-(3-amino-3-oxopropyl)-N'-vinyl imidazolium chloride, N-(4-amino-4-oxobutyl)-N'-vinyl imidazolium chloride, N,N-dimethyl-N-(3-sulfopropyl)-3-(acryloyl amino)-1-propaneammonium inner salt, N,N-diethyl-N-(3-sulfopropyl)-3-(acryloyl amino)-1-propaneammonium inner salt, N,N-dimethyl-N-(4-sulfobutyl)-3-(acryloyl amino)-1-propaneammonium inner salt, N,N-diethyl-N-(4-sulfobutyl)-3-(acryloyl amino)-1-propaneammonium inner salt, N,N-dimethyl-N-(3-sulfopropyl)-2-(acryloyl amino)-1-ethaneammonium inner salt, N,N-diethyl-N-(3-sulfopropyl)-2-(acryloyl amino)-1-ethaneammonium inner salt, N,N-dimethyl-N-(4-sulfobutyl)-2-(acryloyl amino)-1-ethaneammonium inner salt, N,N-diethyl-N-(4-sulfobutyl)-2-(acryloyl amino)-1-ethaneammonium inner salt, and combinations of any two or more thereof.

Examples of suitable olefinic comonomers include, but are not limited to, acrylamide, styrene sulfonic acid, salt of styrene sulfonic acid, N-methylacrylamide, N,N-dimethylacrylamide, acrylic acid, salt of acrylic acid, N-vinylpyrrolidone, methyl acrylate, methacrylate, vinyl sulfonic acid, salt of vinyl sulfonic acid, 2-acrylamido-2-methylpropanesulfonic acid, salt 2-acrylamido-2-methylpropanesulfonic acid, and combinations of any two or more thereof. The salt can be an ammonium salt, an alkali metal salt, or combinations of any two or more thereof.

Some of the olefinic comonomers can be purchased commercially. The others can be synthesized by the process disclosed in the second embodiment of the present invention or in the Examples section.

For example, the olefinic comonomers having the formula of $R_1—C(R_1)=C(R_1)—(C=O)_m—M$ in which M is the same as disclosed above can be prepared from $R_1—C(R_1)=C(R_1)—(C=O)_m—X$ where X is the same as that disclosed above, such as acryloyl chloride, and morpholine or from $R_1—C(R_1)=C(R_1)—(C=O)_m—OH$, such as acrylic acid, and morpholine. The molar ratio of morpholine to the other reactant can be in the range of from about 2:1 to about 1:2. Generally, the reaction can be carried out in an organic solvent such as chloroform or any solvents illustrated above, at a temperature in the range of from about −50° C. to about 20° C., for about 1 to about 10 hours. The reactants are commercially available. See Examples section below for details.

The water-soluble polymers of the third embodiment of the present invention can be prepared by mixing the monomer(s) (i.e., the nitrogen-containing olefinic compounds and the olefinic comonomers), in desired molar ratios if copolymers, terpolymers, or tetrapolymers are desired, in an appropriate liquid medium and then initiating the free-radical polymerization in solution, suspension, or emulsion environment. Generally, any molar ratios can be employed depending on the final polymer desired. The liquid can be an aqueous solution, non-aqueous solution, or mixtures thereof.

Well known compounds commonly employed to initiate free radical polymerization reactions include hydrogen peroxide, azo compounds such as, for example, 2,2'-azobis (2-(2-imidazolin-2-yl)propane) dihydrochloride, alkali metal persulfates such as $K_2S_2O_8$, alkali metal perborates, alkali metal perphosphates, and alkali metal percarbonates. Well known organic peroxide compounds commonly employed to initiate free radical polymerization reactions include lauryl peroxide, 2,5-dimethyl-2,5-bis(2-ethylhexanoylperoxy)hexane, t-butylperoxyprivilate, t-butylperoctoate, p-methane hydroperoxide, and benzoylperoxide. The compound t-butylhyponitrite is a well known alkyl hyponitrite commonly employed to initiate free radical polymerization reactions. Furthermore, ultraviolet light and gamma irradiation are commonly employed to initiate free radical polymerization reactions. In addition, such other method of polymerization as would have occurred to one skilled in the art may be employed, and the present invention is not limited to the particular method of preparing the polymer set out herein. Because the polymerization techniques are well known to one skilled in the art, the description of which is omitted herein for the interest of brevity.

If copolymers, terpolymers, or tetrapolymers are desired, the molar ratio of the nitrogen-containing olefinic monomer to the olefinic comonomer can be any ratio so long as the ratio can produce a polymer that can withstand hostile environment. Generally, the molar ratio can be in the range of from about 0.01:1 to about 100:1, preferably about 0.05:1 to about 50:1, and most preferably 0.1:1 to 30:1. If a combination of the nitrogen-containing olefinic monomers, or the olefinic comonomers, or both are employed, the molar ratios can be any ratio so long as the molar ratio of total nitrogen-containing olefinic monomers to the olefinic comonomers is within the range disclosed above.

According to the fourth embodiment of the present invention, a process which can be used in hydrocarbon-bearing subterranean formations such as water-flooding is provided. The process comprises, or consisting essentially of, or consisting of, introducing a water-soluble composition into a subterranean formation. The water-soluble composition comprises, consists essentially of, or consists of a water-soluble polymer. The scope of the water-soluble polymer is the same as that disclosed in the first embodiment of the present invention, description of which is omitted herein for the interest of brevity.

The term "process" used herein and hereinafter in conjunction with a subterranean formation generally denotes, unless otherwise indicated, a use in drilling fluids, workover fluids, completion fluids, permeability corrections, water or gas coning prevention, fluid loss prevention, matrix acidizing, fracture acidizing, and combinations of any two or more thereof.

The water-soluble composition used in the fourth embodiment of the invention can also comprise a liquid. The term "liquid" used in the present invention denotes water, a solution, a suspension, or combinations thereof wherein the suspension contains dissolved, partially dissolved, or undissolved substances such as salts. The presently preferred liquid is an aqueous liquid such as, for example, fresh water, sea water, salt water, or a produced brine which is defined above.

Examples of salts include metal salts. Generally, the total salts content can vary widely from, for instance, 1 to as high as 30 weight percent (%). The typical salts content can be in the range of from, for instance, about 2 to about 25 weight %.

The introduction of the water-soluble composition into a subterranean formation can be carried out by any methods known to one skilled in the art. Generally the water-soluble polymer can be dissolved, or substantially dissolved, in a liquid so that the water-soluble composition is present in the liquid in an amount, or concentration, sufficient to alter the permeability of a subterranean formation. The amount, or concentration, can be in the range of from about 50 to about 100,000, preferably about 100 to about 50,000, and most preferably 200 to 10,000 mg of the water-soluble composition per liter of the liquid.

The water-soluble composition in a liquid medium can then be introduced, by any means known to one skilled in the art such as pumping, into a subterranean formation so that it can diffuse into the more water-swept portions of the formation. The nature of the formation is not critical to carrying out the process of the present invention. The formation can have a temperature in the range of from about 70° F. to about 400° F., preferably 75° F. to 350° F.

According to the fifth embodiment of the present invention, a gelling composition which can be used in oil field applications is provided. The gelling composition comprises, consists essentially of, or consists of a water-soluble composition, a crosslinking agent, and a liquid. The scope of the water-soluble composition is the same as that disclosed in the third embodiment of the present invention. The liquid component is the same as that disclosed in the fourth embodiment of the present invention.

Any crosslinking agents can be used. For example, a multivalent metallic compound that are capable of crosslinking the gellable carboxylate-containing polymer in the hydrocarbon-bearing formations can be used in the process of the present invention. Examples of suitable multivalent metal compounds include, but are not limited to, $Al^{+3}$, $Cr^{+3}$, $Fe^{+3}$, $Zr^{+4}$, $Ti^{+4}$, and combinations of any two or more thereof.

The presently preferred multivalent metal compound is a metal compound selected from the group consisting of a complexed zirconium compound, a complexed titanium compound, a complexed chromium compound, and combinations of any two or more thereof. Examples of the preferred multivalent metallic compounds include, but are not limited to, zirconium citrate, zirconium complex of hydroxyethyl glycine, ammonium zirconium fluoride, zirconium 2-ethylhexanoate, zirconium acetate, zirconium neodecanoate, zirconium acetylacetonate, tetrakis(triethanolamine)zirconate, zirconium carbonate, ammonium zirconium carbonate, zirconyl ammonium carbonate, zirconium lactate, titanium acetylacetonate, titanium ethylacetoacetate, titanium citrate, titanium triethanolamine, ammonium titanium lactate, aluminum citrate, chromium citrate, chromium acetate, chromium propionate, chromium malonate, and combinations thereof. The presently most preferred crosslinking agent is zirconium lactate, zirconium citrate, tetrakis(triethanolamine)zirconate, or zirconium complex of hydroxyethyl glycine, or combinations thereof. These compounds are commercially available.

According to the fifth embodiment of the present invention, a metallic compound used as a crosslinking agent can also contain a complexing ligand if necessary to further delay the rate of gelation. Preferably, however, the crosslinking agent does not contain such complexing agent. The complexing ligand useful for the present invention to retard the rate of gelation is generally a carboxylic acid containing one or more hydroxyl groups and salts thereof. The complexing ligand can also be an amine that has more than one functional group and contains one or more hydroxyl groups and that can chelate the zirconium or titanium moiety of the zirconium or titanium compounds described above. Examples of suitable complexing ligands include, but are not limited to, hydroxyethyl glycine, lactic acid, ammonium lactate, sodium lactate, potassium lactate, citric acid, ammonium, potassium or sodium citrate, isocitric acid, ammonium, potassium or sodium isocitrate, malic acid, ammonium, potassium or sodium malate, tartaric acid, ammonium, potassium or sodium tartrate, triethanolamine, malonic acid, ammonium, potassium or sodium malonate, and mixtures thereof. The presently preferred complexing ligands are citric acid, lactic acid, tartaric acid and salts thereof, triethanolamine, and hydroxyethyl glycine because of their ready availability and low cost.

A crosslinking agent can also contain two components. The first crosslinking component useful as crosslinking agent is generally water-dispersible or soluble and can be phenol, substituted phenols, aspirin, p-aminobenzoic acid, resorcinol, catechol, hydroquinone, furfuryl alcohol, R'ArO $(CaO)_m$ R', $HOAr(C=O)_m$ OR', HOArOH, R'OArOH, R'OArOR', or combinations of any two or more thereof where Ar is an arylene group which can be non-substituted or substituted; each R' can be the same or different and is each independently selected from the group consisting of hydrogen, carboxylic group, a $C_1$–$C_6$ alkyl, a phenyl group or combinations of any two or more thereof; and m is 0 or 1. The term "water dispersible" used herein is to describe a component that is truly water soluble or is dispersible in water to form a stable suspension. Examples of suitable first crosslinking components include, but are not limited to, phenol, hydroquinone, resorcinol, catechol, p-aminosalicylic acid, p-amino benzoic acid, furfuryl alcohol, phenyl acetate, phenyl propionate, phenyl butyrate, salicylic acid, phenyl salicylate, aspirin, p-hydroxybenzoic acid, methyl p-hydroxybenzoate, methyl o-hydroxybenzoate, ethyl p-hydroxybenzoate, o-hydroxybenzoic acid, hexyl p-hydroxybenzoate, and combinations of any two or more thereof. Presently preferred water dispersible first crosslinking components are phenol, phenyl acetate, phenyl salicylate, methyl p-hydroxybenzoate, resorcinol, catechol, hydroquinone, and combinations of any two or more thereof.

Any water-dispersible or soluble aldehyde, its derivative, or compound that can be converted into aldehyde can be utilized as the second crosslinking component in crosslinking agent. Examples of suitable second crosslinking components include, but are not limited to aliphatic monoaldehydes, aromatic monoaldehydes, aliphatic dialdehydes, aromatic dialdehydes, and their precursors. Preferred aldehydes and their precursors can be selected from the group consisting of formaldehyde, paraformaldehyde, acetaldehyde, propionaldehyde, decanal, glutaraldehyde, terephthaldehyde, hexamethylenetetramine, and combinations of any two or more thereof.

The weight ratio of the water-dispersible first crosslinking component to the second crosslinking component can be any ratio so long as the ratio can effect the gelation of the gelling composition. Generally, such ratio can be in the range of from about 0.01:1 to about 100:1, preferably about 0.1:1 to about 10:1, and most preferably 0.5:1 to 2:1.

Any suitable procedures for preparing the gelling composition can be used. Some of the polymers can require particular mixing conditions, such as slow addition of finely powdered polymer into a vortex of stirred brine, alcohol prewetting, protection from air (oxygen), preparation of stock solutions from fresh rather than salt water, as is known for such polymers.

The concentration or amount of the water-soluble polymer in the gelling composition can range widely and be as suitable and convenient for the various polymers, and for the degree of gelation needed for particular reservoirs. Generally, the concentration of the water-soluble polymer in a liquid is made up to a convenient strength of about 100 to 100,000 mg/l (ppm), preferably about 200 to 70,000 ppm, and most preferably 500 to 50,000 ppm.

The concentration of crosslinking agent used in the present invention depends largely on the concentrations of polymer in the composition. Lower concentrations of polymer, e.g., require lower concentrations of the crosslinking agent. Further, it has been found that for a given concentration of polymer, increasing the concentration of crosslinking agent generally .substantially increases the rate of gelation. The concentration of crosslinking agent in the injected slug varies generally over the broad range of about 1 mg/l (ppm) to about 10,000 ppm, preferably over the range of about 1 ppm to about 7,500 ppm, and most preferably 1 ppm to 2,500 ppm. The liquid generally makes up the rest of the gelling composition.

The concentration of the complexing ligand, if present, in the gelling composition also depends on the concentrations of the water-soluble polymer in the composition and on the desired rate of gelation. Generally, the lower the concentration of the complexing ligand is, the faster the gelation rate is.

According to the sixth embodiment of the present invention, a process which can be used to alter the permeability of a subterranean formation is provided. The process comprises, or consists essentially of, or consists of introducing a gelling composition into a subterranean formation. The scope of the gelling composition is the same as that disclosed in the fifth embodiment of the invention.

The use of gelled polymers to alter the water permeability of underground formations is well known to those skilled in the art. Generally, an aqueous solution containing the polymer and a crosslinker is pumped into the formation so that the solution can enter into the more water swept portions of the formation and alter water permeability by gelling therein.

According to the process of the sixth embodiment of the present invention, an aqueous gelling composition comprising a crosslinking agent and a gellable polymer is injected into an injection or production well. The definition and scope of the crosslinking agent and gellable polymer are the same as those described above. The amount of the aqueous gelling composition introduced or injected can vary widely depending on the treatment volume injected. The amount of the gellable polymer injected is also dependent on the gel strength desired, same as that described for the crosslinking agent.

According to the sixth embodiment of the invention, the gelling can be prepared on the surface followed by introducing the prepared composition into a subterranean formation. Alternatively, individual components of the gelling composition described above can also be simultaneously or sequentially introduced into a subterranean formation.

The nature of the underground formation treated is not critical to the practice of the present invention. The described gelling composition can be introduced or injected into a formation having a temperature range of from about 70° F. to about 350° F. Any means known to one skilled in the art such as, for example, a pump means can be used for introducing or injecting the gelling composition and polymer solution.

According to the seventh embodiment of the invention, a composition which can be used as or in drilling fluids, completion fluids, or workover fluids is provided. The composition can comprise, consist essentially of, or consist of a clay, a water-soluble polymer, a liquid. The definition and scope of liquid and water-soluble polymer are the same as those disclosed above, the description of which are omitted herein for the interest of brevity.

According to the seventh embodiment of the invention, the clay useful in the invention can be any clay. Examples of suitable clays include, but are not limited to, kaolinite, halloysite, vermiculite, chlorite, attapulgite, smectite, montmorillonite, illite, saconite, sepiolite, palygorskite. Fuller's earth, and combinations of any two or more thereof. The presently preferred clay is montmorillonite clay. The presently most preferred clay is sodium montmorillonite, which is also known as bentonite.

Based on the total weight % of the composition, the clay can be present in the composition in the range of from about 0.25 weight % to about 30 weight %, preferably about 0.5 weight % to about 25 weight %, and most preferably 1 weight % to 20 weight %. The water-soluble polymer can be present in the composition in the range of from about 0.005 to about 15; preferably about 0.005 to about 10, more preferably about 0.01 to about 6, and most preferably 0.01 to 3 weight percent of the composition.

The scope and definition of liquid are the same as those disclosed above. The liquid component generally makes up the rest of the composition.

According to the present invention, a thinner can also be present in the present invention, if desired, in an amount in the range of from about 0.001 to about 10 weight %, preferably about 0.001 to about 5 weight %. Examples of suitable thinners include, but are not limited to, phosphates, tannins, modified tannins, lignites, modified lignites, lignosulfonates, polyacrylate polymers, or combinations of any two or more thereof.

According to the seventh embodiment of the invention, if the composition needs to be weighted, the composition can also comprise a weighting agent. Any known weighting agent that can be suspended in the composition can be used in the present invention. Examples of suitable weighting agents include, but are not limited to barite, hematite, calcium carbonate, galena, or combinations of any two or more thereof. The presently preferred weighting agent is barite for it is readily available and effective. Depending on the desired density of the composition, the weighting agent, if present, can be present in the composition in the range of from about 0.0001 to about 70.

Additionally, the composition of the seventh embodiment of the invention can also comprise a variety of other components or additives to obtain a desired property. Examples of the commonly used components or additives include, but are not limited to, viscosifiers, fluid loss control agents, salts, lubricants, surface active agents, flocculants, shale inhibitors, corrosion inhibitors, oxygen scavengers, or combinations of any two or more thereof.

The composition can be prepared by any means known to one skilled in the art such as blending, mixing, etc. Because these means are well known in the art, the description of which is omitted herein for the interest of brevity.

Examples provided hereinbelow are intended to assist one skilled in the art to further understand the invention and should not be considered limitative.

EXAMPLE I

This example illustrates the preparation of nitrogen-containing olefinic monomers.

N-acryloyl morpholine (NAM)

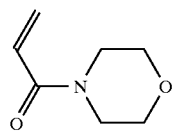

N-acryloyl morpholine was prepared from morpholine and acryloyl chloride. Morpholine (0.35 mole; 30.0 g), 0.42 mole (42.5 g) of triethylamine and 0.1 g of 1,3-dinitrobenzene were dissolved in 350 ml of chloroform and cooled to ca. −15° C. Acryloyl chloride (0.42 mole; 37.8 g) was then added from a dropping funnel in such a way that the temperature in the reaction flask did not exceed 0° C. The reaction mixture was then allowed to reach room temperature (about 25° C). After 2 hours at room temperature the solution was poured into an excess of diethyl ether (500 ml), and the precipitated material was filtered from the ether. The organic phase was concentrated on a rotavapour. Hydroquinone (0.1 g) was added in order to prevent polymerization and then distilled under reduced pressure. The product was immediately placed in the refrigerator. B.p. 74° C./0.01 mbar. The yield was 64%.

N-acryloyl-N'-methyl piperazine (AMP)

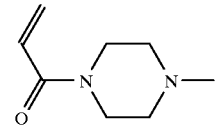

N-acryloyl-N'-methyl piperazine was prepared by adding 0.44 mole (39.8 g) of acryloyl chloride to a solution of 0.40 mole (40.0 g) N-methyl piperazine and 0.1 g hydroquinone in 200 ml of acetonitrile. The addition was carried out in such a way that the temperature in the reaction flask did not exceed 5° C. The reaction mixture was allowed to reach room temperature. A 10 M aqueous NaOH-solution (17.6 g NaOH in 44 ml distilled water, 0.44 mole) was then added and the precipitated material was filtered. The two phases were separated and the organic layer was dried with $CaCl_2$. Distillation under reduced pressure gave the product as a clear liquid. B.p. 90–95° C./0.5 mbar. The yield was 72%.

N-acryloyl-N'-(3-sulfopropyl)-N'-methyl piperazinium inner salt (AMPPS)

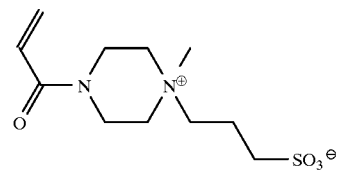

N-acryloyl-N'-(3-sulfopropyl)-N'-methyl piperazinium inner salt was prepared from 0.26 mole (40.1 g) of N-acryloyl-N'-methyl piperazine and 0.29 mole (34.9 g) of 1,3-propanesultone. The reagents were mixed together with 0.1 g of 1,3-dinitrobenzene in 260 ml of acetonitrile. The reaction mixture was heated to 90° C. for 2½ hours. The precipitated material was then filtered and washed three times with diethyl ether (100 ml) each. The white powder was dried under reduced pressure (12 mm Hg) for 18 hours. The yield was 68%.

N-acryloyl-N'-(2-amino-2-oxoethyl)-N'-methyl piperazinium chloride (AOMPC)

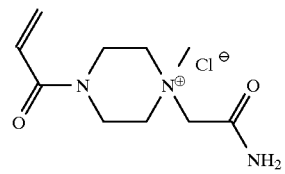

N-acryloyl-N'-methyl piperazine (0.13 mole; 20.0 g) was dissolved in 260 ml of dry acetonitrile (distilled over $P_2O_5$) together with 0.1 g 1,3-dinitrobenzene. Then 0.16 mole (14.6 g) 2-chloro acetamide was added to the N-acryloyl-N'-methyl piperazine, and the mixture was heated to ca. 80° C. for 123 hours. A white, precipitated powder was filtered and washed three times with diethyl ether (150 ml). The product was dried under reduced pressure (12 mm Hg) for 12 hours. The yield was 75%.

N,N-dimethyl-N-(3-sulfopropyl)-N-(4-vinylbenzyl) ammonium inner salt (DMAMSPS)

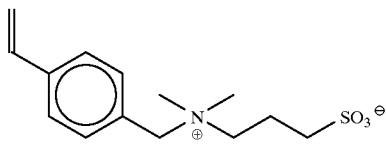

N,N-dimethyl-N-(4-vinylbenzyl) amine (93.0 mmole; 15 g), 111.6 mmole (13.6 g) of 1,3-propanesultone and 0.1 g of 1,3-dinitrobenzene were mixed together and dissolved in 180 ml of toluene. The mixture was heated at 45–50° C. for 72 hours. A white, precipitated material was filtered, washed three times with diethyl ether (100 ml), and finally dried under reduced pressure (11 mm Hg) for 15 hours. The yield was 87%.

N,N-dimethyl-N-(2-amino-2-oxoethyl)-N-(4-vinylbenzyl) ammonium chloride (AODVAC)

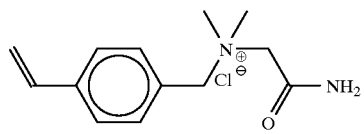

N,N-dimethyl-N-(4-vinylbenzyl) amine (62.0 mmole; 10.0 g), 68.0 mmole (6.4 g) of 2-chloro acetamide and 0.1 g of 1,3-dinitrobenzene were dissolved in 125 ml of acetonitrile and heated at ca. 45° C. for 48 hours. The precipitated material was filtered and washed three times with diethyl ether (100 ml). A white powder was dried under reduced pressure (12 mm Hg) for 16 hours. The yield was 88%.

N-(2-amino-2-oxoethyl)-N'-vinyl imidazolium chloride (AOVC)

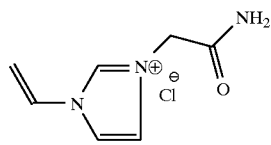

1-Vinyl imidazole (0.17 mole; 15.8 g), 0.20 mole (19.1 g) of 2-chloro acetamide and 0.1 g of 1,3-dinitrobenzene were mixed together, dissolved in 340 ml of acetonitrile and heated at 70–75° C. for three nights (about 64 hours). The precipitated material was then filtered and washed three times with acetonitrile (150 ml). The product was dried under reduced pressure (12 mm Hg) for 15 hours. The product was a white powder, and the yield was 65%.

N,N-dimethyl-N-(3-sulfopropyl)-3-(acryloyl amino)-1-propaneammonium inner salt (APDAPS)

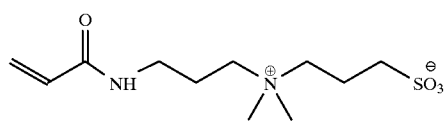

Acryloylchloride (0.70 mole; 63.8 g) and 0.1 g of hydroquinone were dissolved in 350 ml of acetonitrile and cooled to −15° C. Then 0.59 mole (60.0 g) of 3-dimethylamino-1-propylamine was added from a dropping funnel in such a way that the temperature in the reaction flask did not exceed 5° C. The reaction mixture was allowed to reach room temperature. A 10 M aqueous NaOH-solution (28.0 g NaOH in 70 ml distilled water, 0.70 mole) was added and the precipitated material was filtered. The filtrate was concentrated on a rotavapour and then distilled under reduced pressure. B.p. 122° C./0.1 mbar. The yield was 55%.

Eighty-three mmole (13.0 g) of this product was reacted further with 99.6 mmole (12.2 g) of 1,3-propanesultone in 83 ml of toluene. In the mean time, 0.1 g 1,3-dinitrobenzene was added to prevent polymerization. The reaction mixture was heated at ca. 55° C. for 3 hours. A white, precipitated powder was filtered and washed three times with diethyl ether (200 ml). Finally the product was dried under reduced pressure (12 mm Hg) for 17 hours. The yield was 80%.

EXAMPLE II

This example illustrates the production of polymers of the present invention.

Polymerizations were carried out in distilled water or synthetic sea water. For synthetic sea water, one liter distilled water contained 23.83 g NaCl, 0.21 g $NaHCO_3$, 10.77 g $MgCl_2 \cdot 6H_2O$, 1.65 g $CaC_2 \cdot 2H_2O$, and 42.9 g anhydrous $Na_2SO_4$. The monomer solution was 35 weight % and the initiator concentration was 0.3 mole % with respect to total concentration of monomers. The azo-type initiator VA-044 (2,2'-azobis()dihydrochloride) was used to start the polymerizations. The polymerizations were carried out at room temperature. In a typical synthesis, specified quantities of the monomers were dissolved in distilled water or synthetic sea water and the mixture was purged with nitrogen for 50 minutes. Initiator was then added. The polymers were precipitated in methanol or acetone, redissolved in distilled water or synthetic sea water and finally lyophilized (freeze dried). The term "parts" used hereinafter in defining a polymer denotes mole %. The products were white, amorphous powders.

Copolymer Am/AMP

Eighty parts of acrylamide and 20 parts of N-acryloyl-N'-methyl piperazine (AMP) were polymerized in distilled water for 4 hours with use of 0.3 mole % VA-044 as a initiator. The polymer was precipitated in acetone. The yield was 34%.

Copolymer Am/NAM

Eighty parts of acrylamide and 20 parts of N-acryloyl morpholine (NAM) were dissolved in distilled water and the polymerization was carried out with use of 0.3 mol % VA-044 as initiator. The polymerization was stopped after 6 hours. The polymer was precipitated in acetone. The yield was 69%.

Terpolymer Am/NAM/AMP

The polymer was prepared from 70 parts of acrylamide, 15 parts of N-acryloyl morpholine (NAM) and 15 parts of N-acryloyl-N'-methyl piperazine (AMP) with use of 0.3 mole % VA-044 as initiator. Distilled water was used as solvent. After 5 hours the polymer was precipitated in acetone. The yield was 41%.

Copolymer Am/AMPPS

Eighty parts of acrylamide and 20 parts of N-acryloyl-N'-(3-sulfopropyl)-N'-methyl piperazinium inner salt (AMPPS) were polymerized in synthetic sea water for 2 hours with use of 0.3 mole % VA-044 as initiator. The polymer was precipitated in methanol. The yield was 62%.

Copolymer Am/DMAMSPS

A polymer was prepared from 80 parts of acrylamide and 20 parts of N,N-dimethyl-N-(3-sulfopropyl)-N-(4-vinylbenzyl) ammonium inner salt (DMAMSPS) dissolved in synthetic sea water. 0.3 mole % VA-044 was used as initiator. After 4 hours the polymer was precipitated in methanol. The yield was 48%.

Copolymer Am/APDAPS

Eighty parts of acrylamide and 20 parts of N,N-dimethyl-N-(3-sulfopropyl)-3-(acryloylamino)-1-propaneammonium inner salt (APDAPS) were polymerized in synthetic sea water for 5 hours with use of 0.3 mole % VA-044 as initiator. The polymer was precipitated in methanol. The yield was 81%.

Terpolymer Am/AMP/DMAMSPS

Sixty parts of acrylamide, 20 parts of N-acryloyl-N'-methyl piperazine (AMP) and 20 parts of N,N-dimethyl-N-(3-sulfopropyl)-N-(4-vinylbenzyl) ammonium inner salt (DMAMSPS) were dissolved in synthetic sea water and the polymerization was carried out with use of 0.3 mole % VA-044 as initiator.

The polymerization was stopped after 3½ hours by precipitation of the polymer in methanol. The yield was 23%.

Terpolymer Am/AMP/APDAPS

Seventy parts of acrylamide, 25 parts of N-acryloyl-N'-methyl piperazine (AMP) and 5 parts of N,N-dimethyl-N-(3-sulfopropyl)-3-(acryloylamino)-1-propaneammonium inner salt (APDAPS) were polymerized in synthetic sea water with use of 0.3 mole % VA-044 as initiator. The polymerization was stopped after 3 hours by precipitation of the polymer in methanol. The yield was 59%.

Terpolymer Am/AMP/AMPPS

Seventy parts of acrylamide, 15 parts of N-acryloyl-N'-methyl piperazine (AMP) and 15 parts of N-acryloyl-N'-(3-sulfopropyl)-N'-methyl piperazinium inner salt (AMPPS) were dissolved in synthetic sea water and polymerized for 23 hours. VA-044 was used as initiator. The polymer was precipitated in methanol. The yield was 34%.

Copolymer AOMPC/AMPS

Fifty parts of 2-acrylamido-2-methylpropanesulfonic acid (AMPS), 50 parts N-acryloyl-N'-(2-amino-2-oxoethyl)-N'-methyl piperazinium chloride (AOMPC) and 50 parts NaOH were dissolved in NaCl-solution and polymerized for 6 hours with use of 0.3 mole % VA-033 as initiator. The polymer was precipitated in methanol. The yield was 54%.

Terpolymer AOVC/AMP/AMPS

A polymer was prepared from 15 parts of N-(2-amino-2-oxoethyl)-N'-vinyl imidazolium chloride (AOVC), 70 parts of N-acryloyl-N'-methyl piperazine (AMP), 15 parts of 2-acrylamido-2-methylpropane-sulfonic acid (AMPS) and 15 parts of NaOH in synthetic sea water. Three tenths mole % VA-044 was used as initiator and the polymerization was stopped after 5 hours by precipitation of the polymer in methanol. The yield was 38%.

AOMPC Homopolymer.

N-acryloyl-N'-(2-amino-2-oxoethyl)-N'-methyl piperazinium chloride (AOMPC) (20.19 mmol) was dissolved in synthetic sea water and 0.3 mole % VA-044 was added. The polymerization was stopped after 6 hours by precipitation of the polymer in acetone. The yield was 57%.

Terpolymer Am/AMP/AMPS

Seventy parts of acrylamide, 15 parts of N-acryloyl-N'-methyl piperazine (AMP) and 15 parts of 2-acrylamido-2-methyl-propanesulfonic acid (AMPS) were dissolved in distilled water and polymerized for 3 hours. Three tenths mole % VA-044 was used as initiator. The polymer was precipitated in acetone. The yield was 47%.

EXAMPLE III

This example illustrates the preparation of gelling compositions from the polymers disclosed above and the stability of gels formed from the gelling compositions.

Preparation of Gelling Compositions

Stock solutions of a polymer contained 4 weight % of the polymer in synthetic sea water. The polymer solution was allowed to stand at least three nights (about 64 hours) with magnetic stirring before use.

Stock solutions of phenol, formaldehyde and HMTA each containing 10,000 mg/l (ppm) were used.

For each test 4.0 g of gelling composition were made by adding polymer, phenol and formaldehyde/HMTA solution and diluting with synthetic sea water to the correct concentration. The same ppm concentration of both phenol and formaldehyde/HMTA was used. Magnetic stirring was used to mix the gelling compositions. After mixing the pH of the gelling compositions were registered using pH indicator strips. The pH of the was not adjusted in any way. The gelling compositions were thereafter transferred to glass vials, and the solutions were flushed with argon gas for 5 minutes before the vials were closed. The glass vials were weighed before and after adding gelling compositions.

For aging at 120° C., the glass vials were placed in stainless steel containers filled with water. After aging at 120° C., the stainless steel containers were cooled down to room temperature, the gel strength of the samples were characterized visually as weak, strong or rigid. The syneresis of the gels were measured as (weight of gel after exposure)/(initial weight of gel forming solution).

For gels in ampules, the syneresis was measured by measuring the gel height and the length of the liquid layer after ageing.

Measurement Inherent Viscosity

Polymer solution (0.1 weight %) in synthetic sea water was made for viscosity measurements. The polymer solution was allowed to stand for 3 days with magnetic stirring. Before viscosity measurement the polymer solution was filtered through a 5 vm Millipore filter. The relative viscosity of the 0.1 weight % polymer solution (relative to synthetic sea water) was measured with an Ubbelhode viscosimeter with an inner capillary diameter of 0.69 mm. At least 3 parallel measurements were performed for each solution. The temperature of the polymer solution under the viscosity measurement was 25.0±0.05° C.

Relative viscosity:=time for polymer solution through capillary/time for synthetic sea water trough capillary Inherent viscosity: ln(rel. visc.)/0.1 g/dl The results are shown in the following Tables I–XXI. These tables show that gels formed from the polymers of the present invention were resistant to high temperature and high salinity environment. Little or no syneresis was observed after prolonged aging at high temperature and high salinity environment.

TABLE I

| Run No. | Am/AMP[a] Feed Ratio[b] | Inherent Viscosity dl/g | Polymer conc. (ppm) in SNSW[c] | Phenol/ HMTA[d] (ppm of each) | Gel height (G) and Liquid height (L) after aging at 120° C. in SNSW for | | |
|---|---|---|---|---|---|---|---|
| | | | | | 30 days | 55 days | 70 days |
| 181 JSI II 23 | 80/20 | 5.4 | 6200 | 2500 | G = 25 mm L – 5 mm Rigid | G = 25 mm L = 5 mm Rigid | G = 25 L = 5 mm Rigid |
| 181 JSI II 23 | 80/20 | 5.4 | 10400 | 2500 | G = 30 mm L = 0 mm Rigid | G = 25 mm L = 5 mm Rigid | G = 25 mm L = 5 mm Rigid |
| 181 JSI II 23 | 80/20 | 5.4 | 20000 | 2500 | G = 26 mm L = 0 mm Rigid | G - 24 mm L = 1 mm Rigid | G = 24 mm L = 2 mm Rigid |

[a]Am = acrylamide, AMP = N-acryloyl-N'-methyl piperazine
[b]mole % ratio of monomers in the aqueous solution
[c]SNSW = synthetic sea water
[d]HMTA = hexamethylenetetramine

TABLE II

| Run No. | Am/AMP[a] Feed Ratio[b] | Inherent Viscosity dl/g | Polymer conc. (ppm) in SNSW[c] | Phenol/ HMTA[d] (ppm of each) | Weight % gel[e] Gel Character 5 months |
|---|---|---|---|---|---|
| 181 HSI II 23 | 80/20 | 5.4 | 6200 | 2500 | 80 Rigid |
| 181 JSI II 23 | 80/20 | 5.4 | 10400 | 2500 | 80 Rigid |
| 181 JSI II 23 | 80/20 | 5.4 | 20000 | 2500 | 90 Rigid |

[a]Am = acrylamide, AMP = N-acryloyl-N'-methyl piperazine
[b]mole % ratio of monomers in the aqueous solution
[c]SNSW = synthetic sea water
[d]HMTA = hexamethylenetetramine
[e]Weight % gel of initial weight of the solution after aging at 120° C. in synthetic sea water

TABLE III

| Run No. | Am/AMP[a] Feed Ratio[b] | Inherent Viscosity dl/g | Polymer conc. (ppm) in SNSW[c] | Phenol/ HCHO[d] (ppm of each) | Weight % gel[e] Gel Character | |
|---|---|---|---|---|---|---|
| | | | | | 5 days | 30 days |
| 154 TOB VII 43 | 70/30 | 5.1 | 20000 | 2500 | | 100 Strong |
| 168 JSI I 76 | 70/30 | 3.8 | 10000 | 500 | | 55 Weak |
| 168 JSI I 76 | 70/30 | 3.8 | 20000 | 2500 | | 100 Rigid |
| 155 TOB VII 52 | 60/40 | 4.3 | 20000 | 2500 | | 100 Strong |
| 155 TOB VII 52 | 60/40 | 4.3 | 5000 | 1000 | | 82 Rigid |
| 155 TOB VII 52 | 60/40 | 4.3 | 10000 | 1000 | | 100 Strong |
| 155 TOB VII 52 | 60/40 | 4.3 | 10000 | 2000 | | 100 Rigid |
| 156 TOB VII 49 | 50:50 | 3.4 | 20000 | 2500 | | 100 Weak |
| 156 TOB VII 49 | 50/50 | 3.5 | 5000 | 1000 | | 83 Strong |
| 156 TOB VII 49 | 50/50 | 3.5 | 10000 | 1000 | | 89 Strong |
| 156 TOB VII 49 | 50/50 | 3.5 | 10000 | 2500 | | 100 Rigid |

[a]Am = acrylamide, AMP = N-acryloyl-N'-methyl piperazine
[b]mole % ratio of monomers in the aqueous solution
[c]SNSW = synthetic sea water
[d]HCHO = formaldehyde
[e]Weight % gel of initial weight of the solution after aging at 120° C. in synthetic sea water

TABLE IV

| Run No. | Am/AMP[a] Feed Ratio[b] | Inherent Viscosity dl/g | Polymer conc. (ppm) in SNSW[c] | Phenol[d]/ HMTA[e] (ppm) | Weight % gel[f] Gel Character 30 days |
|---|---|---|---|---|---|
| 154 TOB VII 43 | 70/30 | 5.1 | 10000 | 2000 | 96 Strong |
| 154 TOB VII 43 | 70/30 | 5.1 | 20000 | 2000 | 100 Strong |
| 168 JSI I 76 | 70/30 | 3.8 | 5000 | 1000 | 61 Strong |

TABLE IV-continued

| Run No. | Am/AMP[a] Feed Ratio[b] | Inherent Viscosity dl/g | Polymer conc. (ppm) in SNSW[c] | Phenol[d]/ HMTA[e] (ppm) | Weight % gel[f] Gel Character 30 days |
|---|---|---|---|---|---|
| 168 JSI I 76 | 70:30 | 3.8 | 10000 | 500 | 73 Weak |
| 168 JSI I 76 | 70:30 | 3.8 | 10000 | 1000 | 80 Weak |
| 155 TOB VII 52 | 60/40 | 4.3 | 10000 | 2000 | 92 Weak |
| 155 TOB VII 52 | 60/40 | 4.3 | 20000 | 2000 | 100 Strong |
| 197 JSI II 63 | 60/40 | 3.8 | 20000 | 2500 | 100 Rigid |
| 197 JSI II 63 | 60/40 | 3.8 | 10000 | 2500 | 90 Rigid |
| 198 JSI II 65 | 60/40 | 3.7 | 20000 | 2500 | 100 Rigid |
| 156 TOB VII 49 | 50/50 | 3.5 | 20000 | 2000 | 100 Weak |

[a]Am = acrylamide, AMP = N-acryloyl-N'-methyl piperazine
[b]mole % ratio of monomers in the aqueous solution
[c]SNSW = synthetic sea water
[d]2500 ppm
[e]HMTA = hexamethylenetetramine
[f]Weight % gel of initial weight of the solution after aging at 120° C. in synthetic sea water

TABLE V

| Run No. | AM/NAM[a] Feed Ratio[b] | Inherent Viscosity dl/g | Polymer conc. (ppm) in SNSW[c] | Phenol/ HMTA[d] (ppm of each) | Gel height (G) and Liquid height (L) after aging at 120° C. in SNSW for | | |
|---|---|---|---|---|---|---|---|
| | | | | | 30 days | 55 days | 70 days |
| 179 JSI II 11 | 80:20 | 4.4 | 5400 | 2500 | G = 30 mm L = 5 mm Rigid | G = 28 mm L = 7 mm Rigid | G = 28 mm L = 7 mm Rigid |
| 179 JSI II 11 | 80:20 | 4.4 | 10300 | 2400 | G = 27 mm L = 5 mm Rigid | G = 27 mm L = 5 mm Rigid | G = 27 mm L = 5 mm Rigid |
| 179 JSI II 11 | 80:20 | 4.4 | 20000 | 2400 | G = 26 mm L = 3 mm Rigid | G = 34 mm L = 5 mm Rigid | G = 24 mm L = 5 mm Rigid |

[a]Am = acrylamide, NAM = N-acryloyl morpholine
[b]mole % ratio of monomers in the aqueous solution
[c]SNSW = synthetic sea water
[d]HMTA = hexamethylenetetramine

TABLE VI

| Run No. | Am/NAM[a] Feed Ratio[b] | Inherent Viscosity dl/g | Polymer conc. (ppm) in SNSW[c] | Phenol/ HMTA[d] (ppm of each) | Weight % gel[e] Gel Character 5 months |
|---|---|---|---|---|---|
| 179 JSI II 11 | 80/20 | 4.4 | 5400 | 2500 | 0.8 Rigid |
| 179 JSI II 11 | 80/20 | 4.4 | 10300 | 2400 | 0.9 Rigid |
| 179 JSI II 11 | 80/20 | 4.4 | 20000 | 2400 | 0.9 Rigid |

[a]Am = acrylamide, NAM = N-acryloyl morpholine
[b]mole % ratio of monomers in the aqueous solution
[c]SNSW = synthetic sea water
[d]HMTA = hexamethylenetetramine
[e]Weight % gel of initial weight of the solution after aging at 120° C. in synthetic sea water

TABLE VII

| Run No. | Am/NAM[a] Feed Ratio[b] | Inherent Viscosity dl/g | Polymer conc. (ppm) in SNSW[c] | Phenol/ HCHO[d] (ppm of each) | Weight % gel[e] Gel Character |
|---|---|---|---|---|---|
| 170 JSI I 79 | 80/20 | 6.2 | 10000 | 500 | 30 Strong |
| 170 JSI I 79 | 80/20 | 6.2 | 10000 | 2500 | 28 Strong |
| 171 JSI I 81 | 70/30 | 3.7 | 10000 | 1000 | 100 Rigid |
| 172 JSI I 83 | 60/40 | 3.3 | 20000 | 1000 | 92 Rigid |
| 71 TOB V 85 | 20/80 | 2.5 | 20000 | 2500 | 100 Strong / 70 Strong |
| 125 TOB VII 17 | 20/80 | 1.1 | 30000 | 4000 | 42 Strong / 35 Strong |

TABLE VII-continued

| Run No. | Am/NAM[a] Feed Ratio[b] | Inherent Viscosity dl/g | Polymer conc. (ppm) in SNSW[c] | Phenol/ HCHO[d] (ppm of each) | Weight % gel[e] Gel Character |
|---|---|---|---|---|---|
| 125 TOB VII 17 | 20/80 | 1.1 | 30000 | 2000 | 55 Strong |

[a]Am = acrylamide, NAM = N-acryloyl morpholine
[b]mole % ratio of monomers in the aqueous solution
[c]SNSW = synthetic sea water
[d]HCHO = formaldehyde
[e]Weight % gel of initial weight of the solution after aging at 120° C. in synthetic sea water

TABLE VIII

| Run No. | Am/NAM[a] Feed Ratio[b] | Inherent Viscosity dl/g | Polymer conc. (ppm) in SNSW[c] | Phenol[d]/ HMTA[e] (ppm) | Weight % gel[f] Gel Character 30 days | |
|---|---|---|---|---|---|---|
| | | | | | Parallel 1[g] | Parallel 2[g] |
| 150 JSI I 59 | 70/30 | 2.2 | 20000 | 2000 | 93 Rigid | 94 Weak |
| 150 JSI I 59 | 70/30 | 2.2 | 10000 | 2000 | 100 Rigid | |
| 151 JSI I 61 | 60/40 | 2.2 | 20000 | 2000 | 96 Rigid | 80 Weak |
| 152 JSI I 63 | 50/50 | 2.5 | 20000 | 2000 | 90 Strong | 100 Weak |

[a]Am = acrylamide, NAM = N-acryloyl morpholine
[b]mole % ratio of monomers in the aqueous solution
[c]SNSW = synthetic sea water
[d]2500 ppm
[e]HMTA = hexamethylenetetramine
[f]Weight % gel of initial weight of the solution after aging at 120° C. in synthetic sea water

TABLE IX

| Run No. | Am/NAM/ AMP[a] Feed Ratio[b] | Inherent Viscosity dl/g | Polymer conc. (ppm) in SNSW[c] | Phenol/ HMTA[d] (ppm of each) | Weight % gel[e] Gel Character 30 days |
|---|---|---|---|---|---|
| 188 JSI II 21 | 70/15/15 | 4.6 | 10000 | 2500 | 100 Rigid |
| 188 JSI II 21 | 70/15/15 | 4.6 | 20000 | 2500 | 95 Rigid |
| 188 JSI II 21 | 70/15/15 | 4.6 | 10000 | 1000 | 47 Strong |

[a]Am = acrylamide, NAM = N-acryloyl morpholine, AMP = N-acryloyl-N'-methyl piperazine
[b]mole % ratio of monomers in the aqueous solution
[c]SNSW = synthetic sea water
[d]HMTA = hexamethylenetetramine
[e]Weight % gel of initial weight of the solution after aging at 120° C. in synthetic sea water

TABLE X

| Run No. | Am/ AMPPS[a] Feed Ratio[b] | Inherent Viscosity dl/g | Polymer conc. (ppm) in SNSW[c] | Phenol/ HCHO[d] (ppm of each) | Weight % gel[e] Gel Character | |
|---|---|---|---|---|---|---|
| | | | | | 5 days | 30 days |
| 162 JSI I 65 | 80/20 | 2.2 | 10000 | 2500 | 100 Strong | |
| 162 JSI I 65 | 80/20 | 2.2 | 20000 | 1000 | 100 Rigid | |
| 162 JSI I 65 | 80/20 | 2.2 | 10000 | 2000 | 100 Rigid | |
| 132 JSI I 28 | 80/20 | 1.8 | 30000 | 4000 | 100 Rigid | 41 Strong |
| 132 JSI I 28 | 70/30 | 1.8 | 30000 | 2000 | | 32 Strong |
| 130 JSI I 26 | 60/40 | 1.6 | 30000 | 4000 | 100 Strong | 62 Strong |
| 130 JSI I 26 | 60/40 | 1.6 | 30000 | 2000 | | 75 Strong |
| 100 TOB VI 68 | 50/50 | | 20000 | 2500 | 94 Weak | 60 Weak |
| 120 TOB VII 15 | 50/40 | 1.5 | 30000 | 4000 | 100 Strong | 88 Strong |
| 120 TOB VII 15 | 50/50 | 1.5 | 30000 | 2000 | | 77 Strong |

[a]Am = acrylamide, AMPPS = N-acryloyl-N'-(3-sulfopropyl)-N'-methyl piperazinium inner salt
[b]mole % ratio of monomers in the aqueous solution
[c]SNSW = synthetic sea water
[d]HCHO = formaldehyde
[e]Weight % gel of initial weight of the solution after aging at 120° C. in synthetic sea water

TABLE XI

| Run No. | Am/AMPPS[a] Feed Ratio[b] | Inherent Viscosity dl/g | Polymer conc. (ppm) in SNSW[c] | Phenol/ HMTA[d] (ppm of each) | Weight % gel[e] Gel Character 30 days |
|---|---|---|---|---|---|
| 202 JSI II 67 | 80/20 | 3.5 | 10000 | 2500 | Rigid 90 |
| 202 JSI II 67 | 80/20 | 3.5 | 20000 | 2500 | Rigid 70 |

[a]Am = acrylamide, AMPPS = N-acryloyl-N'-(3-sulfopropyl)-N'-methyl piperazinium inner salt
[b]mole % ratio of monomers in the aqueous solution
[c]SNSW = synthetic sea water
[d]HMTA = hexamethylenetetramine
[e]Weight % gel of initial weight of the solution after aging at 120° C. in synthetic sea water

TABLE XII

| Run No. | Am/ DMAMSPS[a] Feed Ratio[b] | Inherent Viscosity dl/g | Polymer conc. (ppm) in SNSW[c] | Phenol/ HCHO[d] (ppm of each) | Weight % gel[e] Gel Character | |
|---|---|---|---|---|---|---|
| | | | | | 5 days | 30 days |
| 149 JSI | 90/10 | 1.0 | 10000 | 2500 | | 81 Strong |

TABLE XII-continued

| Run No. | Am/ DMAMSPS[a] Feed Ratio[b] | Inherent Viscosity dl/g | Polymer conc. (ppm) in SNSW[c] | Phenol/ HCHO[d] (ppm of each) | Weight % gel[e] Gel Character 5 days | 30 days |
|---|---|---|---|---|---|---|
| 149 JSI I 55 | 90/10 | 1.0 | 20000 | 2500 | | 88 Strong |
| 65 TOB V 79 | 80/20 | 0.9 | 10000 | 2500 | 100 Weak | 79 Weak |
| 137 TOB VII 23 | 80/20 | 2.0 | 30000 | 4000 | 93 Strong | 72 Strong |
| 137 TOB VII 23 | 80/20 | 2.0 | 10000 | 1000 | | 77 Strong |
| 137 TOB VII 23 | 80/20 | 2.0 | 10000 | 2500 | | 100 Rigid |

[a]Am = acrylamide, DMAMSPS = N,N-dimethyl-N-(3-sulfopropyl)-N-(4-vinylbenzyl)-ammonium inner salt
[b]mole % ratio of monomers in the aqueous solution
[c]SNSW = synthetic sea water
[d]HCHO = formaldehyde
[e]Weight % gel of initial weight of the solution after aging at 120° C. in synthetic sea water

TABLE XIII

| Run No. | Am/DMAMSPS[a] Feed Ratio[b] | Inherent Viscosity dl/g | Polymer conc. (ppm) in SNSW[c] | Phenol/ HMTA[d] (ppm of each) | Weight % gel[e] Gel Character 30 days |
|---|---|---|---|---|---|
| 137 TOB VII 23 | 80/20 | 2.0 | 10000 | 2000 | 81 Weak gel |
| 137 TOB VII 23 | 80/20 | 2.0 | 20000 | 2000 | 100 Weak |

[a]Am = acrylamide, DMAMSPS = N,N-dimethyl-N-(3-sulfopropyl)-N-(4-vinylbenzyl)-ammonium inner salt
[b]mole % ratio of monomers in the aqueous solution
[c]SNSW = synthetic sea water
[d]HMTA = hexamethylenetetramine
[e]Weight % gel of initial weight of the solution after aging at 120° C. in synthetic sea water

TABLE XIV

| Run No. | Am/APDAPS[a] Feed Ratio[b] | Inherent Viscosity dl/g | Polymer conc. (ppm) in SNSW[c] | Phenol/ HMTA[d] (ppm of each) | Weight % gel[e] Gel Character 30 days |
|---|---|---|---|---|---|
| 193 TOB VII 89 | 80/20 | 5.3 | 5000 | 2500 | 80 Rigid |
| 193 TOB VII 89 | 80/20 | 5.3 | 10000 | 2500 | 80 Rigid |
| 193 TOB VII 89 | 80/20 | 5.3 | 20000 | 2500 | 90 Strong |

[a]Am = acrylamide, APDAPS = N,N-dimethyl-N-(3-sulfopropyl)-3-(acryloylamino)-1-propaneammonium inner salt
[b]mole % ratio of monomers in the aqueous solution
[c]SNSW = synthetic sea water
[d]HMTA = hexamethylenetetramine
[e]Weight % gel of initial weight of the solution after aging at 120° C. in synthetic sea water

TABLE XV

| Run No. | Am/AMP/ DMAMSPS[a] Feed Ratio[b] | Inherent Viscos- ity dl/g | Polymer conc. (ppm) in SNSW[c] | Phenol/ HCHO[d] (ppm of each) | Phenol/ HMTA[e] (ppm of each) | Weight % gel[f] Gel Character 30 days |
|---|---|---|---|---|---|---|
| 195 TOB VII 87 | 60/20/20 | 2.4 | 10000 | 2500 | | 100 Strong |
| 195 TOB VII 87 | 60/20/20 | 2.4 | 20000 | 2500 | | 100 Rigid |
| 195 TOB VII 87 | 60/20/20 | 2.4 | 20000 | | 2500 | 100 Rigid |

[a]Am = acrylamide, AMP = N-acryloyl-N'-methyl piperazine, DMAMSPS = N,N-dimethyl-N-(3-sulfopropyl)-N-(4-vinylbenzyl-ammonium inner salt
[b]mole % ratio of monomers in the aqueous solution
[c]SNSW = synthetic sea water
[d]HCHO = formaldehyde
[e]HMTA = hexamethylenetetramine
[f]Weight % gel of initial weight of the solution after aging at 120° C. in synthetic sea water

TABLE XVI

| Run No. | Am/AMP/ APDAPS[a] Feed Ratio[b] | Inherent Viscosity dl/g | Polymer conc. (ppm) in SNSW[c] | Phenol/ HMTA[d] (ppm of each) | Weight % gel[e] Gel Character 30 days |
|---|---|---|---|---|---|
| 196 TOB VII 85 | 70/25/5 | 4.4 | 5000 | 2500 | 100 Rigid |
| 196 TOB VII 85 | 70/25/5 | 4.4 | 10000 | 2500 | 83 Rigid |
| 196 TOB VII 85 | 70/25/5 | 4.4 | 20000 | 2500 | 86 Rigid |
| 203 IBV I 49 | 60/30/10 | 3.5 | 10000 | 2500 | 85 Rigid |
| 203 IBV I 49 | 60/30/10 | 3.5 | 20000 | 2500 | 85 Rigid |

[a]Am = acrylamide, AMP = N-acryloyl-N'-methyl piperazine, APDAPS = N,N-dimethyl-N-(3-sulfopropyl)-3-(acryloylamino)-1-propaneammonium inner salt
[b]mole % ratio of monomers in the aqueous solution
[c]SNSW = synthetic sea water
[d]HMTA = hexamethylenetetramine
[e]Weight % gel of initial weight of the solution after aging at 120° C. in synthetic sea water

TABLE XVII

| Run No. | Am/AMP/ APDAPS[a] Feed Ratio[b] | Inherent Viscosity dl/g | Polymer conc. (ppm) in SNSW[c] | Phenol/ HMTA[d] (ppm of each) | Weight % gel[e] Gel Character 30 days |
|---|---|---|---|---|---|
| 184 JSI II 25 | 70/15/15 | 1.9 | 10000 | 2500 | 70 Rigid |
| 184 JSI II 25 | 70/15/15 | 1.9 | 20000 | 2500 | 100 Rigid |

[a]Am = acrylamide, AMP = N-acryloyl-N'-methyl piperazine, AMPPS = N-acryloyl-N'-(3-sulfopropyl)-N'-methyl piperazinium inner salt
[b]mole % ratio of monomers in the aqueous solution
[c]SNSW = synthetic sea water

TABLE XVII-continued

| Run No. | Am/AMP/ APDAPS[a] Feed Ratio[b] | Inherent Viscosity dl/g | Polymer conc. (ppm) in SNSW[c] | Phenol/ HMTA[d] (ppm of each) | Weight % gel[e] Gel Character 30 days |
|---|---|---|---|---|---|

[d]HMTA = hexamethylenetetramine
[e]Weight % gel of initial weight of the solution after aging at 120° C. in synthetic sea water

TABLE XVIII

| Run No. | AOMPC/ AMPS[a] Feed Ratio[b] | Inherent Viscosity dl/g | Polymer conc. (ppm) in SNSW[c] | Phenol/ HCHO[d] (ppm of each) | Weight % gel[e] Gel Character 30 days |
|---|---|---|---|---|---|
| 189 IBV I 43 | 50/50 | 1.1 | 10000 | 2500 | 100 Strong |

[a]AOMPC = N-acryloyl-N'-(2-amino-2-oxoethyl)-N'-methyl piperazinium chloride, AMPS = 2-acrylamido-2-methyl-propanesulfonic acid
[b]mole % ratio of monomers in the aqueous solution
[c]SNSW = synthetic sea water
[d]HCHO = formaldehyde
[e]Weight % gel of initial weight of the solution after aging at 120° C. in synthetic sea water

TABLE XIX

| Run No. | AOVC/AMP/ AMPS[a] Feed Ratio[b] | Inherent Viscosity dl/g | Polymer conc. (ppm) in SNSW[c] | Phenol/ HCHO[d] (ppm of each) | Weight % gel[e] Gel Character 30 days |
|---|---|---|---|---|---|
| 191 JSI II 33 | 15/70/15 | 1.6 | 20000 | 2500 | 100 Rigid |

[a]AOVC = N-(2-amino-2-oxoethyl)-N'-vinyl imidazolium chloride, AMP = N-acryloyl-N'-methyl piperazine, AMPS = 2-acrylamido-2-methyl-propanesulfonic acid
[b]mole % ratio of monomers in the aqueous solution
[c]SNSW = synthetic sea water
[d]HCHO = formaldehyde
[e]Weight % gel of initial weight of the solution after aging at 120° C. in synthetic sea water

TABLE XX

| Run No. | AOMPC Homopol[a] | Inherent Viscosity dl/g 0.1 weight % | Polymer conc. (ppm) in SNSW[b] | Phenol/ HCHO[c] (ppm of each) | Weight % gel[d] Gel Character 30 days |
|---|---|---|---|---|---|
| 117 TOB VII 8 | | 1.4 | 30000 | 4000 | 100 Strong |

[a]AOMPC = N-acryloyl-N'-(2-amino-2-oxoethyl)-N'-methyl piperazinium chloride, homopolymer
[b]SNSW = synthetic sea water
[c]HCHO = formaldehyde
[d]Weight % gel of initial weight of the solution after aging at 120° C. in synthetic sea water

TABLE XXI

| Run No. | Am/AMP/ AMPS[a] Feed Ratio[b] | Inherent Viscosity dl/g | Polymer conc. (ppm) in SNSW[c] | Phenol/ HCHO[d] (ppm of each) | Weight % gel[e] Gel Character 30 days |
|---|---|---|---|---|---|
| 157 TOB VII 57 | 50/25/25 | 3.4 | 20000 | 1000 | 100 Strong |
| 157 TOB VII 57 | 50/25/25 | 3.4 | 20000 | 2500 | 100 Strong |

[a]Am = acrylamide, AMP = N-acryloyl-N'-methyl piperazine, AMPS = 2 = acrylamido-2-methyl-propanesulfonic acid
[b]mole % ratio of monomers in the aqueous solution
[c]SNSW = synthetic sea water
[d]HCHO = formaldehyde
[e]Weight % gel of initial weight of the solution after aging at 120° C. in synthetic sea water

EXAMPLE IV

This example is a comparative example showing that gels formed from a commonly employed polyacrylamide do not withstand well under a hostile environment condition as compared to the gels formed from the invention polymers.

A 7000 ppm solution of Dowell J333 polyacrylamide in seawater was crosslinked with phenol and formaldehyde at 120° C. Table XXII shows a summary of the results.

TABLE XXII

| Polymer Concentration | Phenol/ Formaldehyde (ppm of each) | Gel Height (G) and Liquid Height (L) after 6 days aging at 120° C. | | |
|---|---|---|---|---|
| | | G (mm) | L (mm) | |
| 7000 | 500 | 22 | 65 | Rigid |
| 7000 | 1000 | 20 | 70 | Rigid |
| 7000 | 2000 | 30 | 75 | Rigid |

The results shown in Table XXII indicate that much syneresis occurred in gels formed from polyacrylamide only after aging for 6 days.

EXAMPLE V

This example illustrates a fresh water based composition of the invention that can be used as drilling fluids, completion fluids, or workover fluids.

Seven fresh water based compositions were prepared by mixing the components shown in Table XXIII on a Multi-mixer in quart jars. The mixing time, in minutes, after the addition of each component is shown in the table. After the mixing was completed, the fluid compositions were transferred into pint jars and then tested initially for viscosity and gel strength according to the API RP 13B-1, First Edition, Jun. 1, 1990 procedure. The compositions were then mixed for five minutes and tested for filtration according to the low-temperature/low-pressure test procedure. These test results are presented in Table XXIV under "Initial Results". The compositions were then kept in capped jars at 75 ° C. for about 16 hours, cooled to about 30° C., and tested after the compositions were mixed for 5 minutes. These test results are represented in Table XXIV under "Results After Aging at 75° C.".

TABLE XXIII[a]

| Run | Materials Used |
|---|---|
| 8-1 | 345 ml tap water + 10 g bentonite (40) |
| 8-2 | 325 ml tap water + 10 g bentonite (20) + 20 g of 4% solution of NAM/AM in deionized water (20). |
| 8-3 | 325 ml tap water + 10 g bentonite (20) + 20 g of 4% solution of NAM/AP in deionized water (20). |
| 8-4 | 325 ml tap water + 10 g bentonite (20) + 20 g of 4% solution of NAM/AA in deionized water (20). |
| 8-5 | 305 ml tap water + 10 g bentonite (20) + 40 g of 4% solution of NAM/AM in deionized water (20). |
| 8-6 | 305 ml tap water + 10 g bentonite (20) + 40 g of 4% solution of NAM/AP in deionized water (20). |
| 8-7 | 305 ml tap water + 10 g bentonite (20) + 40 g of 4% solution of NAM/AA in deionized water (20). |

[a]NAM/AM is a copolymer of 25% (mole %) acryloyl morpholine and 75% acrylamide; NAM/AP is a copolymer of 25% acryloyl morpholine and 75% acrylamide-2-methylpropanesulfonate; NAM/AA is a copolymer of 25% acryloyl morpholine and 75% acrylate; these polymers were prepared according to the process disclosed in Example II.

TABLE XXIV[a]

| | Initial Results | | | | | Results After Aging at 75° C. | | | | |
|---|---|---|---|---|---|---|---|---|---|---|
| Run | AV | PV | YP | Gels | FL | AV | PV | YP | Gels | FL |
| 8-1 | 2.5 | 2 | 1 | 1/1 | 20.4 | 2.5 | 2 | 1 | 1/2 | 16.8 |
| 8-2 | 12.0 | 6 | 12 | 3/5 | 63.7 | 14.5 | 5 | 19 | 3/6 | 67.6 |
| 8-3 | 8.0 | 7 | 2 | 1/3 | 15.8 | 8.5 | 7 | 3 | 2/2 | 15.4 |
| 8-4 | 10.5 | 8 | 5 | 1/3 | 13.5 | 11.5 | 10 | 3 | 2/3 | 13.1 |
| 8-5 | 32.5 | 19 | 27 | 14/23 | 68.1 | 33.0 | 19 | 28 | CNM | 47.4 |
| 8-6 | 24.0 | 13 | 22 | 3/5 | 7.8 | 25.0 | 15 | 20 | 3/5 | 9.0 |
| 8-7 | 36.0 | 21 | 30 | 5/6 | 8.3 | 37.0 | 23 | 28 | 5/6 | 8.6 |

[a]AV—apparent viscosity, cps
PV—plastic viscosity, cps.
Gels—gel strength, 10 seconds/10 minutes, lbs/100 sq. ft.
FL—fluid loss at low-temperature/low-pressure, ml 30 minutes.
CNM—can not be measured accurately.

The results in Table XXIV show that the four inventive fluid compositions (runs 8-3, 8-4, 8-6, and 8-7) had much lower fluid loss than the fluid composition of run 8-1 that represents a base fluid which did not contain any polymer. Further, these four inventive compositions had higher viscosity than the base fluid. High viscosity is desirable. Even though two inventive compositions (run 8-2 and 8-5) had high fluid loss, their high viscosity is useful in bringing the drill cuttings to the surface.

EXAMPLE VI

This example illustrates a sea water based composition of the invention that can be used as drilling fluids, completion fluids, or workover fluids.

Four sea water based compositions were prepared by mixing the components shown in Table XXV on a Multi-mixer in quart jars. The mixing time, in minutes, after the addition of each component is shown in the table. After the mixing was completed, the fluid compositions were kept at about 75° C. for about two hours. Each composition was mixed 5 minutes and after adding 0.05 ml of octyl alcohol as a defoamer to each composition, each sample was tested initially for viscosity, gel strength, and filtration at low-temperature/low-pressure according to the API RP 13B-1, First Edition, Jun. 1, 1190 procedure. These test results are presented in Table XXVI under "Initial Results". The compositions were then kept in capped jars at 75° C. for about 16 hours and cooled to about 30° C. Next, the compositions were mixed 5 minutes and, after adding 0.05 ml of octyl alcohol as a defoamer to each composition, they were retested. These results are represented in Table XXVI under "Results After Aging at 75° C.". The composition of sea water is shown in Example II.

TABLE XXV[a]

| Run | Materials Used |
|---|---|
| 9-1 | 340 ml tap water + 10 g bentonite (20) + 2 g Na-lignite (10) + 14.7 g sea salt (30) |
| 9-2 | 265 ml tap water + 10 g bentonite (20) + 2 g Na-lignite (10) + 14.7 g sea salt (10) + 75 g of 4% solution of NAM/AM in deionized water (20) |
| 9-3 | 265 ml tap water + 10 g bentonite (20) + 2 g Na-lignite (10) + 14.7 g sea salt (10) + 75 g of 4% solution of NAM/AP in deionized water (20) |
| 9-4 | 265 ml tap water + 10 g bentonite (20) + 2 g Na-lignite (10) + 14.7 g sea salt (10) + 75 g of 4% solution of NAM/AA in deionized water (20) |

[a]See footnote a in Table XXIII.

TABLE XXVI[a]

| | Initial Results | | | | | Results After Aging at 75° C. | | | | |
|---|---|---|---|---|---|---|---|---|---|---|
| Run | AV | PV | YP | Gels | FL | AV | PV | YP | Gels | FL |
| 9-1 | 6.5 | 2 | 9 | 8/9 | 79.2 | 7.0 | 3 | 8 | 6/8 | 62.2 |
| 9-2 | 16.5 | 10 | 13 | 5/8 | 19.4 | 15.0 | 10 | 10 | 4/8 | 18.5 |
| 9-3 | 24.0 | 15 | 18 | 6/9 | 8.1 | 22.5 | 14 | 17 | 4/7 | 7.6 |
| 9-4 | 28.5 | 18 | 21 | 4/15 | 4.8 | 24.5 | 16 | 17 | 3/10 | 4.8 |

[a]AV—apparent viscosity, cps
PV—plastic viscosity, cps.
Gels—gel strength, 10 seconds/10 minutes, lbs/100 sq. ft.
FL—fluid loss at low-temperature/low-pressure, ml 30 minutes.

The results in Table XXVI show that three inventive fluid compositions (runs 9-2, 9-3, and 9-4) had much lower fluid loss than the fluid composition of run 9-1 that represents a base fluid which did not contain any polymer. Furthermore, these three inventive compositions also had higher viscosity than the base fluid. High viscosity is useful in bringing the drill cuttings to the surface.

The results shown in the above examples clearly demonstrate that the present invention is well adapted to carry out the objects and attain the ends and advantages mentioned as well as those inherent therein. While modifications may be made by those skilled in the art, such modifications are encompassed within the spirit of the present invention as defined by the disclosure and the claims.

That which is claimed:

1. A composition comprising a clay, a polymer, and a liquid wherein said polymer comprises repeat units derived from a nitrogen-containing olefinic monomer having the formula selected from the group consisting of

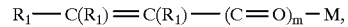

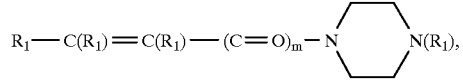

-continued

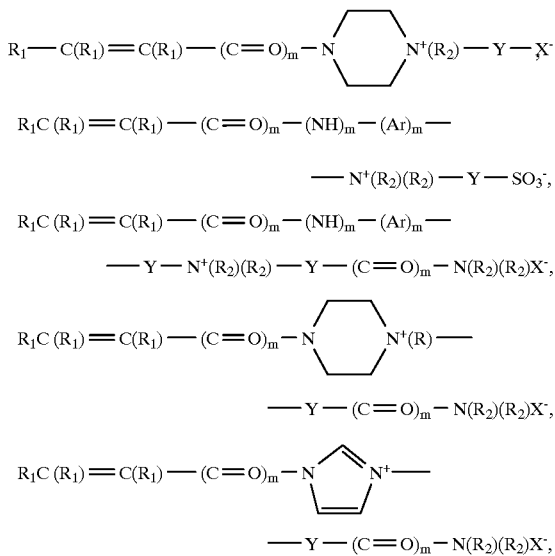

and combinations of any two or more thereof wherein
each $R_1$ and $R_2$ are the same or different and are independently selected from the group consisting of hydrogen, alkyl radical, aryl radical, aralkyl radical, alkaryl radical, and combinations of any two or more thereof wherein each radical contains 1 to about 30 carbon atoms;
X is an anion selected from the group consisting of halide, sulfate, phosphate, nitrate, sulfonate, phosphonates, sulfinate, phosphinate, and combinations of any two or more thereof;
each Y is independently selected from the group consisting of alkylene radical, phenylene group, imidazolium group, naphthylene group, biphenylene group, and combinations of any two or more thereof;
Ar is an arylene group; and
each m is independently 0 or 1.

2. A composition according to claim 1 wherein said polymer further comprises repeat units derived from at least one olefinic comonomer having the formula selected from the group consisting of $R_1$—C($R_1$)=C($R_1$)—W, $R_1$—C($R_1$)=C($R_1$)—(C=O)$_m$—Z, $R_1$—C($R_1$,)=C($R_1$)—Y—W, $R_1$—C($R_1$)=C($R_1$)—(C=O)$_m$—N($R_2$)—Y—$R_2$, $R_1$—C($R_1$)=C($R_1$)—(C=O)$_m$—G—Y—Z, $R_1$C($R_1$)=C($R_1$)—(C=O)$_m$—G—Y—W, $R_1$—C($R_1$)=C($R_1$)—(C=O)$_m$—Y—Z, and combinations of any two or more thereof wherein
each $R_1$ and $R_2$ are the same or different and are independently selected from the group consisting of hydrogen, alkyl radical, aryl radical, aralkyl radical, alkaryl radical, and combinations of any two or more thereof,
each m is independently 0 or 1;
Z has the formula selected from the group consisting of N($R_2$)($R_2$), N$^+$($R_2$)($R_2$)($R_2$)X$^-$ in which X is an anion selected from the group consisting of halide, sulfate, phosphate, nitrate, sulfonate, phosphonates, sulfinate, phosphinate, and combinations of any two or more thereof;
G is N($R_2$) or O;
each Y is independently selected from the group consisting of alkylene radical, phenylene group, imidazolium group, naphthylene group, biphenylene group, and combinations of two or more thereof; and
W is an acid moiety selected from the group consisting of phosphinic acid, phosphonic acid, sulfinic acid, sulfonic acid, sulfuric acid, sulfurous acid, carboxylic acid, phosphoric acid, ammonium salt or alkali metal salt of any of these acids, and combinations of any two or more thereof.

3. A composition according to claim 1 wherein said polymer further comprises repeat units derived from at least one olefinic comonomer having the formula selected from the group consisting of $R_1$—C($R_1$)=C($R_1$)—(C=O)$_m$—Z, $R_1$—C($R_1$)=C($R_1$)—(C=O)$_m$—Y—W, $R_1$—C($R_1$)=C($R_1$)—W, $R_1$—C($R_1$)=C($R_1$)—(C=O)—G—Y—W, and combinations of any two or more thereof wherein
each $R_1$ is the same or different and is independently selected from the group consisting of hydrogen, alkyl radical, aryl radical, aralkyl radical, alkaryl radical, and combinations of any two or more thereof;
each m is independently 0 or 1;
Z has the formula selected from the group consisting of N($R_2$)($R_2$), N$^+$($R_2$)($R_2$)($R_2$)X$^-$ in which X is an anion selected from the group consisting of halide, sulfate, phosphate, nitrate, sulfonate, phosphonates, sulfinate, phosphinate, and combinations of any two or more thereof;
G is N($R_1$) or O;
each Y is independently selected from the group consisting of alkylene radical, phenylene group, imidazolium group, naphthylene group, biphenylene group, and combinations of two or more thereof; and
W is an acid moiety selected from the group consisting of phosphinic acid, phosphonic acid, sulfinic acid, sulfonic acid, sulfinic acid, sulfurous acid, carboxylic acid, phosphoric acid, ammonium salt or alkali metal salt of any of these acids, and combinations of any two or more thereof.

4. A composition according to claim 1 wherein said nitrogen-containing olefinic monomer is selected from the group consisting of N-acryloyl morpholine, N-acryloyl-N'-methyl piperazine, N-acryloyl-N'-ethyl piperazine, N-acryloyl-N'-propyl piperazine, N-acryloyl-N'-sulfopropyl)-N'-methyl piperazinium inner salt, N-acryloyl-N'-(3-sulfopropyl)-N'-ethyl piperazinium inner salt, N-acryloyl-N'-(4-sulfopropyl)-N'-methyl piperazinium inner salt, N-acryloyl-N'-(4-sulfopropyl)-N'-ethyl piperazinium inner salt, N-acryloyl-N'-(2-amino-2-oxoethyl)-N'-methyl piperazinium chloride, N-acryloyl-N'-(3-amino-3-oxopropyl)-N'-methyl piperazinium chloride, N-acryloyl-N'-(4-amino-4-oxobutyl)-N'-methyl piperazinium chloride, N-acryloyl-N'-(2-amino-2-oxoethyl)-N'-ethyl piperazinium chloride, N-acryloyl-N'-(3-amino-3-oxopropyl)-N'-ethyl piperazinium chloride, N-acryloyl-N'-(4-amino-4-oxobutyl)-N'-ethyl piperazinium chloride, N,N-dimethyl-N-(3-sulfopropyl)-N-(4-vinylbenzyl) ammonium inner salt, N,N-dimethyl-N-(4-sulfobutyl)-N-(4-vinylbenzyl) ammonium inner salt, N,N-diethyl-N-(3-sulfopropyl)-N-(4-vinylbenzyl) ammonium inner salt, N,N-diethyl-N-(4-sulfobutyl)-N-(4-vinylbenzyl) ammonium inner salt, N,N-dimethyl-N-(3-sulfopropyl)-N-(3-vinylbenzyl) ammonium inner salt, N,N-dimethyl-N-(4-sulfobutyl)-N-(3-vinylbenzyl) ammonium inner salt, N,N-diethyl-N-(3-sulfopropyl)-N-(3-vinylbenzyl) ammonium inner salt, N,N- diethyl-N-(4-sulfobutyl)-N-(3-vinylbenzyl) ammonium inner salt, N,N-dimethyl-N-(2-amino-2-oxoethyl)-N-(4-vinylbenzyl) ammonium chloride, N,N-diethyl-N-(2-amino-2-oxoethyl)-N-(4-vinylbenzyl) ammonium chloride, N,N-dimethyl-N-(3-amino-3-oxopropyl)-N-(4-vinylbenzyl) ammonium chloride, N,N-diethyl-N-(3-amino-3-oxopropyl)-N-(4-vinylbenzyl) ammonium chloride, N,N-dimethyl-N-(2-amino-2-oxoethyl)-N-(3-vinylbenzyl) ammonium chloride, N,N-diethyl-N-(2-amino-2-oxoethyl)-N-(3-vinylbenzyl) ammonium chloride, N,N-dimethyl-N-(3-amino-3-oxopropyl)-N-(3-vinylbenzyl) ammonium chloride, N,N-diethyl-N-(3-amino-3-oxopropyl)-N-(3-vinylbenzyl) ammonium chloride, N-(2-amino-2-oxoethyl)-N'-vinyl imidazolium chloride, N-(3-amino-3-oxopropyl)-N'-vinyl imidazolium chloride, N-(4-amino-4-oxobutyl)-N'-vinyl imidazolium chloride, N,N-dimethyl-N-(3-sulfopropyl)-3-(acryloyl amino)-1-propaneammonium inner salt, N,N-diethyl-N-(3-sulfopropyl)-3-(acryloyl amino)-1-propaneammonium inner salt, N,N-dimethyl-N-(4-sulfobutyl)-3-(acryloyl amino)-1-propaneammonium inner salt, N,N-diethyl-N-(4-sulfobutyl)-3-(acryloyl amino)-1-propaneammonium inner salt, N,N-dimethyl-N-(3-sulfopropyl)-2-(acryloyl amino)-1-ethaneammonium inner salt, N,N-diethyl-N-(3-sulfopropyl)-2-(acryloyl amino)-1-ethaneammonium inner salt, N,N-dimethyl-N-(4-sulfobutyl)-2-(acryloyl amino)-1-ethaneamronium inner salt, N,N-diethyl-N-(4-sulfobutyl)-2-(acryloyl amino)-1-ethaneammonium inner salt, and combinations of any two or more thereof.

5. A composition according to claim 1 wherein said nitrogen-containing olefinic monomer is selected from the group consisting of N,N-dimethyl-N-(3-sulfopropyl)-N-(4-vinylbenzyl) ammonium inner salt, N,N-dimethyl-N-(3-sulfobutyl)-N-(4-vinylbenzyl) ammonium inner salt, N,N-diethyl-N-(3-sulfopropyl)-N-(4-vinylbenzyl) ammonium inner salt, N,N-diethyl-N-(3-sulfobutyl)-N-(4-vinylbenzyl) ammonium inner salt, N,N-dimethyl-N-(3-sulfopropyl)-N-(3-vinylbenzyl) ammonium inner salt, N,N-dimethyl-N-(3-sulfobutyl)-N-(3-vinylbenzyl) ammonium inner salt, N,N-diethyl-N-(3-sulfopropyl)-N-(3-vinylbenzyl) ammonium inner salt, N,N-diethyl-N-(3-sulfobutyl)-N-(3-vinylbenzyl) ammonium inner salt, N-acryloyl-N'-methyl-N'-(2-amino-2-oxoethyl) piperazinium chloride, N-acryloyl-N'-methyl-N'-(3-amino-3-oxopropyl) piperazinium chloride, N-acryloyl-N'-methyl-N'-(4-amino-4-oxobutyl) piperazinium chloride, N-acryloyl-N'-ethyl-N'-(2-amino-2-oxoethyl) piperazinium chloride, N-acryloyl-N'-ethyl-N'-(3-amino-3-oxopropyl) piperazinium chloride, N-acryloyl-N'-ethyl-N'-(4-amino-4-oxobutyl) piperazinium chloride, N,N-dimethyl-N-(2-amino-2-oxoethyl)-N-(4-vinylbenzyl) ammonium chloride, N,N-diethyl-N-(2-amino-2-oxoethyl)-N-(4-vinylbenzyl) ammonium chloride, N,N-dimethyl-N-(3-amino-3-oxopropyl)-N-(4-vinylbenzyl) ammonium chloride, N,N-diethyl-N-(3-amino-3-oxopropyl)-N-(4-vinylbenzyl) ammonium chloride, N-(2-amino-2-oxoethyl)-N'-vinylimidazolium chloride, N-(3-amino-3-oxopropyl)-N'-vinylimidazolium chloride, N-(4-amino-4-oxobutyl)-N'-vinylimidazolium chloride, and combinations of any two or more thereof.

6. A composition according to claim 3 wherein said nitrogen-containing olefinic monomer is selected from the group consisting of N-acryloyl morpholine, N-acryloyl-N'-methyl piperazine, N-acryloyl-N'-ethyl piperazine, N-acryloyl-N'-propyl piperazine, N-acryloyl-N'-(3-sulfopropyl)-N'-methyl piperazinium inner salt, N-acryloyl-N'-(3-sulfopropyl)-N'-ethyl piperazinium inner salt, N-acryloyl-N'-(4-sulfopropyl)-N'-methyl piperazinium inner salt, N-acryloyl-N'-(4-sulfopropyl)-N'-ethyl piperazinium inner salt, N-acryloyl-N'-(2-amino-2-oxoethyl)-N'-methyl piperazinium chloride, N-acryloyl-N'-(3-amino-3-oxopropyl)-N'-methyl piperazinium chloride, N-acryloyl-N'-(4-amino-4-oxobutyl)-N'-methyl piperazinium chloride, N-acryloyl-N'-(2-amino-2-oxoethyl)-N'-ethyl piperazinium chloride, N-acryloyl-N'-(3-amino-3-oxopropyl)-N'-ethyl piperazinium chloride, N-acryloyl-N'-(4-amino-4-oxobutyl)-N'-ethyl piperazinium chloride, N,N-dimethyl-N-(3-sulfopropyl)-N-(4-vinylbenzyl) ammonium inner salt, N,N-dimethyl-N-(4-sulfobutyl)-N-(4-vinylbenzyl) ammonium inner salt, N,N-diethyl-N-(3-sulfopropyl)-N-(4-vinylbenzyl) ammonium inner salt, N,N-diethyl-N-(4-sulfobutyl)-N-(4-vinylbenzyl) ammonium inner salt, N,N-dimethyl-N-(3-sulfopropyl)-N-(3-vinylbenzyl) ammonium inner salt, N,N-dim ethyl-N-(4-sulfobutyl)-N-(3-vinylbenzyl) ammonium inner salt, N,N-diethyl-N-(3-sulfopropyl)-N-(3-vinylbenzyl) ammonium inner salt, N,N-diethyl-N-(4-sulfobutyl)-N-(3-vinylbenzyl) ammonium inner salt, N,N-dimethyl-N-(2-amino-2-oxoethyl)-N-(4-vinylbenzyl) ammonium chloride, N,N-diethyl-N-(2-amino-2-oxoethyl)-N-(4-vinylbenzyl) ammonium chloride, N,N-dimethyl-N-(3-amino-3-oxopropyl)-N-(4-vinylbenzyl) ammonium chloride, N,N-diethyl-N-(3-amino-3-oxopropyl)-N-(4-vinylbenzyl) ammonium chloride, N,N-dimethyl-N-(2-amino-2-oxoethyl)-N-(3-vinylbenzyl) ammonium chloride, N,N-diethyl-N-(2-amino-2-oxoethyl)-N-(3-vinylbenzyl) ammonium chloride, N,N-dimethyl-N-(3-amino-3-oxopropyl)-N-(3-vinylbenzyl) ammonium chloride, N,N-diethyl-N-(3-amino-3-oxopropyl)-N-(3-vinylbenzyl) ammonium chloride, N-(2-amino-2-oxoethyl)-N'-vinyl imidazolium chloride, N-(3-amino-3-oxopropyl)-N'-vinyl imidazolium chloride, N-(4-amino-4-oxobutyl)-N'-vinyl imidazolium chloride, N,N-dimethyl-N-(3-sulfopropyl)-3-(acryloyl amino)-1-propaneammonium inner salt, N,N-diethyl-N-(3-sulfopropyl)-3-(acryloyl amino)-1-propaneammonium inner salt, N,N-dimethyl-N-(4-sulfobutyl)-3-(acryloyl amino)-1-propaneammonium inner salt, N,N-diethyl-N-(4-sulfobutyl)-3-(acryloyl amino)-1-propaneammonium inner salt, N,N-dimethyl-N-(3-sulfopropyl)-2-(acryloyl amino)-1-ethaneammonium inner salt, N,N-diethyl-N-(3-sulfopropyl)-2-(acryloyl amino)-1-ethaneammonium inner salt, N,N-dimethyl-N-(4-sulfobutyl)-2-(acryloyl amino)-1-ethaneammonium inner salt, N,N-diethyl-N-(4-sulfobutyl)-2-(acryloyl amino)-1-ethaneammonium inner salt, and combinations of any two or more thereof.

7. A composition according to claim 3 wherein said nitrogen-containing olefinic monomer has the formula selected from the group consisting of N,N-dimethyl-N-(3-sulfopropyl)-N-(4-vinylbenzyl) ammonium inner salt, N,N-dimethyl-N-(3-sulfobutyl)-N-(4-vinylbenzyl) ammonium inner salt, N,N-diethyl-N-(3-sulfopropyl)-N-(4-vinylbenzyl) ammonium inner salt, N,N-diethyl-N-(3-sulfobutyl)-N-(4-vinylbenzyl) ammonium inner salt, N,N-dimethyl-N-(3- sulfopropyl)-N-(3-vinylbenzyl) ammonium inner salt, N,N-dimethyl-N-(3-sulfobutyl)-N-(3-vinylbenzyl) ammonium inner salt, N,N-diethyl-N-(3-sulfopropyl)-N-(3-vinylbenzyl) ammonium inner salt, N,N-diethyl-N-(3-sulfobutyl)-N-(3-vinylbenzyl) ammonium inner salt, N-acryloyl-N'-methyl-N'-(2-amino-2-oxoethyl) piperazinium chloride, N-acryloyl-N'-methyl-N'-(3-amino-3-oxopropyl) piperazinium chloride, N-acryloyl-N'-methyl-N'-(4-amino-4-oxobutyl) piperazinium chloride, N-acryloyl-N'-ethyl-N'-(2-amino-2-oxoethyl) piperazinium chloride, N-acryloyl-N'-ethyl-N'-(3-amino-3-oxopropyl) piperazinium chloride, N-acryloyl-N'-ethyl-N'-(4-amino-4-oxobutyl) piperazinium chloride, N,N-dimethyl-N-(2-amino-2-oxoethyl)-N-(4-vinylbenzyl) ammonium chloride, N,N-diethyl-N-(2-amino-2-oxoethyl)-N-(4-vinylbenzyl) ammonium chloride, N,N-dimethyl-N-(3-amino-3-oxopropyl)-N-(4-vinylbenzyl) ammonium chloride, N,N-diethyl-N-(3-amino-3-oxopropyl)-N-(4-vinylbenzyl) ammonium chloride, N-(2-amino-2-oxoethyl)-N'-vinylimidazolium chloride, N-(3-amino-3-oxopropyl)-N'-vinylimidazolium chloride, N-(4-amino-4-oxobutyl)-N'-vinylimidazolium chloride, and combinations of any two or more thereof.

8. A composition according to claim 3 wherein said nitrogen-containing olefinic monomer is N-acryloyl-N'-methyl piperazine.

9. A composition according to claim 3 wherein said nitrogen-containing olefinic monomer is N-acryloyl-N'-(3-sulfopropyl)-N'-methyl piperazinium inner salt.

10. A composition according to claim 3 wherein said nitrogen-containing olefinic monomer is N-acryloyl-N'-(2-amino-2-oxoethyl)-N'-methyl piperazinium chloride.

11. A composition according to claim 3 wherein said nitrogen-containing olefinic monomer is N,N-dimethyl-N-(3-sulfopropyl)-N-(4-vinylbenzyl) ammonium inner salt.

12. A composition according to claim 3 wherein said nitrogen-containing olefinic monomer is N,N-dimethyl-N-(2-amino-2-oxoethyl)-N-(4-vinylbenzyl) ammonium chloride.

13. A composition according to claim 3 wherein said nitrogen-containing olefinic monomer is N-(2-amino-2-oxoethyl)-N'-vinyl imidazolium chloride.

14. A composition according to claim 3 wherein said nitrogen-containing olefinic monomer is N,N-dimethyl-N-(3-sulfopropyl)-3-(acryloyl amino)-1-propaneammonium inner salt.

15. A composition according to claim 3 wherein said nitrogen-containing olefinic monomer is N-acryloylmorpholine.

16. A composition according to claim 3 wherein said olefinic comonomer is selected from the group consisting of acrylamide, styrene sulfonic acid, salt of styrene sulfonic acid, N-methylacrylamide, N,N-dimethylacrylamide, acrylic acid, salt of acrylic acid, N-vinylpyrrolidone, methyl acrylate, methacrylate, vinyl sulfonic acid, salt of vinyl sulfonic acid, 2-acrylamido-2-methylpropanesulfonic acid, salt of 2-acrylamido-2-methylpropanesulfonic acid, and combinations of any two or more thereof.

17. A composition according to claim 16 wherein said olefinic comonomer is acrylamide.

18. A composition comprising a clay, a water-soluble polymer, and a liquid wherein said polymer comprises repeat units derived from at least one nitrogen-containing olefinic monomer and at least one olefinic comonomer;

said nitrogen-containing olefinic monomer has a formula selected from the group consisting of

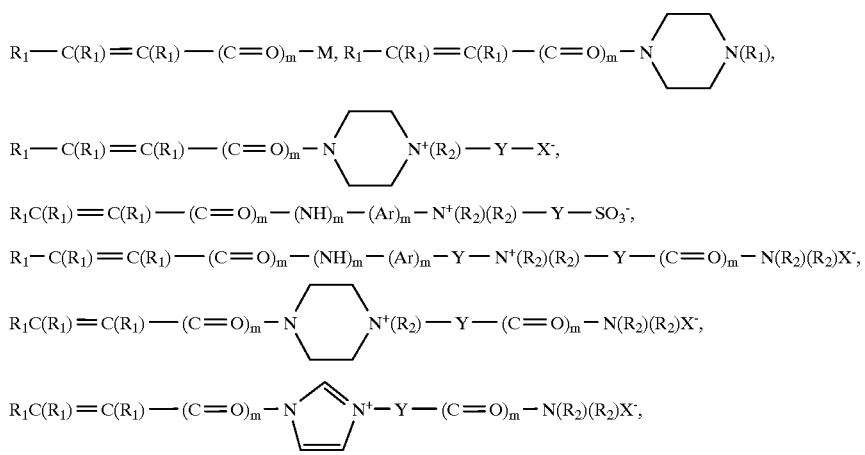

and combinations of any two or more thereof and said olefinic comonomer has the formula selected from the group consisting of $R_1$—$C(R_1)$=$C(R_1)$—W, $R_1$—$C(R_1)$=$C(R_1)$—$(C$=$O)_m$—Z, $R_1$—$C(R_1)$=$C(R_1)$—Y—W, $R_1$—$C(R_1)$=$C(R_1)$—$(C$=$O)_m$—$N(R_2)$—Y—$R_2$, $R_1$—$C(R_1)$=$C(R_1)$—$(C$=$O)_m$—G—Y—Z, $R_1C(R_1)$=$C(R_1)$—$(C$=$O)_m$—G—Y—W, $R_1$—$(R_1)$=$C(R_1)$—$(C$=$O)_m$—Y—Z wherein $R_1$ and $R_2$ are each independently selected from the group consisting of hydrogen, alkyl radical, aryl radical, aralkyl radical, alkaryl radical, and combinations of any two or more thereof wherein each radical contains 1 to about 30 carbon atoms;

M is a substituted or unsubstituted morpholine group;

each Y is independently selected from the group consisting of alkylene radical, phenyl group, imidazolium group, naphthyl group, biphenyl group, and combinations of any two or more thereof;

Ar is an arylene group;

G is $N(R_1)$ or O;

Z has the formula selected from the group consisting of $N(R_2)(R_2)$, $N^+(R_2)(R_2)(R_2)X^-$, and combinations of any two or more thereof;

X is an anion selected from the group consisting of halide, sulfate, phosphate, nitrate, sulfonate, phosphonates, sulfinate, phosphinate, and combinations of any two or more thereof;

each m is independently 0 or 1; and

W is an acid moiety selected from the group consisting of phosphinic acid, phosphonic acid, sulfinic acid, sulfonic acid, sulfuric acid, sulfurous acid, carboxylic acid, phosphoric acid, ammonium salt or alkali metal salt of any of these acids, and combinations of any two or more thereof.

19. A composition according to claim 18 wherein said nitrogen-containing olefinic monomer is selected from the group consisting of N-acryloyl morpholine, N-acryloyl-N'-methyl piperazine, N-acryloyl-N'-ethyl piperazine, N-acryloyl-N'-propyl piperazine, N-acryloyl-N'-(3-sulfopropyl)-N'-methyl piperazinium inner salt, N-acryloyl-N'-(3-sulfopropyl)-N'-ethyl piperazinium inner salt, N-acryloyl-N'-(4-sulfopropyl)-N'-methyl piperazinium inner salt, N-acryloyl-N'-(4-sulfopropyl)-N'-ethyl piperazinium inner salt, N-acryloyl-N'-(2-amino-2-oxoethyl)-N'-methyl piperazinium chloride, N-acryloyl-N'-(3-amino-3-oxopropyl)-N'-methyl piperazinium chloride, N-acryloyl-N'-(4-amino-4-oxobutyl)-N'-methyl piperazinium chloride, N-acryloyl-N'-(2-amino-2-oxoethyl)-N'-ethyl piperazinium chloride, N-acryloyl-N'-(3-amino-3-oxopropyl)-N'-ethyl piperazinium chloride, N-acryloyl-N'-(4-amino-4-oxobutyl)-N'-ethyl piperazinium chloride, N,N-dimethyl-N-(3-sulfopropyl)-N-(4-vinylbenzyl) ammonium inner salt, N,N-dimethyl-N-(4-sulfobutyl)-N-(4-vinylbenzyl) ammonium inner salt, N,N-diethyl-N-(3-sulfopropyl)-N-(4-vinylbenzyl) ammonium inner salt, N,N-diethyl-N-(4-sulfobutyl)-N-(4-vinylbenzyl) ammonium inner salt, N,N-dimethyl-N-(3-sulfopropyl)-N-(3-vinylbenzyl) ammonium inner salt, N,N-diethyl-N-(4-sulfobutyl)-N-(3-vinylbenzyl) ammonium inner salt, N,N-diethyl-N-(3-sulfopropyl)-N-(3-vinylbenzyl) ammonium inner salt, N,N-diethyl-N-(4-sulfobutyl)-N-(3-vinylbenzyl) ammonium inner salt, N,N-dimethyl-N-(2-amino-2-oxoethyl)-N-(4-vinylbenzyl) ammonium chloride, N,N-diethyl-N-(2-amino-2-oxoethyl)-N-(4-vinylbenzyl) ammonium chloride, N,N-dimethyl-N-(3-amino-3-oxopropyl)-N-(4-vinylbenzyl) ammonium chloride, N,N-diethyl-N-(3-amino-3-oxopropyl)-N-(4-vinylbenzyl) ammonium chloride, N,N-dimethyl-N-(2-amino-2-oxoethyl)-N-(3-vinylbenzyl) ammonium chloride, N,N-diethyl-N-(2-amino-2-oxoethyl)-N-(3-vinylbenzyl) ammonium chloride, N,N-dimethyl-N-(3-amino-3-oxopropyl)-N-(3-vinylbenzyl) ammonium chloride, N,N-diethyl-N-(3-amino-3-oxopropyl)-N-(3-vinylbenzyl) ammonium chloride, N-(2-amino-2-oxoethyl)-N'-vinyl imidazolium chloride, N-(3-amino-3-oxopropyl)-N'-vinyl imidazolium chloride, N-(4-amino-4-oxobutyl)-N'-vinyl imidazolium chloride, N,N-dimethyl-N-(3-sulfopropyl)-3-(acryloyl amino)-1-propaneammonium inner salt, N,N-diethyl-N-(3-sulfopropyl)-3-(acryloyl amino)-1-propaneammonium inner salt, N,N-dimethyl-N-(4-sulfobutyl)-3-(acryloyl amino)-1-propaneammonium inner salt, N,N-diethyl-N-(4-sulfobutyl)-3-(acryloyl amino)-1-propaneammonium inner salt, N,N-dimethyl-N-(3-sulfopropyl)-2-(acryloyl amino)-1-ethaneammonium inner salt, N,N-diethyl-N-(3-sulfopropyl)-2-(acryloyl amino)-1-ethaneammonium inner salt, N,N-dimethyl-N-(4-sulfobutyl)-2-(acryloyl amino)-1-ethaneammonium inner salt, N,N-diethyl-N-(4-sulfobutyl)-2-(acryloyl amino)-1-ethaneammonium inner salt, and combinations of any two or more thereof.

20. A composition according to claim 18 wherein said nitrogen-containing olefinic monomer is selected from the group consisting of N,N-dimethyl-N-(3-sulfopropyl)-N-(4-vinylbenzyl) ammonium inner salt, N,N-dimethyl-N-(3-sulfobutyl)-N-(4-vinylbenzyl) ammonium inner salt, N,N-diethyl-N-(3-sulfopropyl)-N-(4-vinylbenzyl) ammonium inner salt, N,N-diethyl-N-(3-sulfobutyl)-N-(4-vinylbenzyl) ammonium inner salt, N,N-dimethyl-N-(3-sulfopropyl)-N-(3-vinylbenzyl) ammonium inner salt, N,N-dimethyl-N-(3-sulfobutyl)-N-(3-vinylbenzyl) ammonium inner salt, N,N-diethyl-N-(3-sulfopropyl)-N-(3-vinylbenzyl) ammonium inner salt, N,N-diethyl-N-(3-sulfobutyl)-N-(3-vinylbenzyl) ammonium inner salt, N-acryloyl-N'-methyl-N'-(2-amino-2-oxoethyl) piperazinium chloride, N-acryloyl-N'-methyl-N'-(3-amino-3-oxopropyl) piperazinium chloride, N-acryloyl-N'-methyl-N'-(4-amino-4-oxobutyl) piperazinium chloride, N-acryloyl-N'-ethyl-N'-(2-amino-2-oxoethyl) piperazinium chloride, N-acryloyl-N'-ethyl-N'-(3-amino-3-oxopropyl) piperazinium chloride, N-acryloyl-N'-ethyl-N'-(4-amino-4-oxobutyl) piperazinium chloride, N,N-dimethyl-N-(2-amino-2-oxoethyl)-N-(4-vinylbenzyl) ammonium chloride, N,N-diethyl-N-(2-amino-2-oxoethyl)-N-(4-vinylbenzyl) ammonium chloride, N,N-dimethyl-N-(3-amino-3-oxopropyl)-N-(4-vinylbenzyl) ammonium chloride, N,N-diethyl-N-(3-amino-3-oxopropyl)-N-(4-vinylbenzyl) ammonium chloride, N-(2-amino-2-oxoethyl)-N'-vinylimidazolium chloride, N-(3-amino-3-oxopropyl)-N'-vinylimidazolium chloride, N-(4-amino-4-oxobutyl)-N'-vinylimidazolium chloride, and combinations of any two or more thereof.

21. A composition according to claim 18 wherein said nitrogen-containing olefinic monomer is N-acryloyl-N'-methyl piperazine.

22. A composition according to claim 18 wherein said nitrogen-containing olefinic monomer is N-acryloyl-N'-(3-sulfopropyl)-N'-methyl piperazinium inner salt.

23. A composition according to claim 18 wherein said nitrogen-containing olefinic monomer is N-acryloyl-N'-(2-amino-2-oxoethyl)-N'-methyl piperazinium chloride.

24. A composition according to claim 18 wherein said nitrogen-containing olefinic monomer is N,N-dimethyl-N-(3-sulfopropyl)-N-(4-vinylbenzyl) ammonium inner salt.

25. A composition according to claim 18 wherein said nitrogen-containing olefinic monomer is N,N-dimethyl-N-(2-amino-2-oxoethyl)-N-(4-vinylbenzyl) ammonium chloride.

26. A composition according to claim 18 wherein said nitrogen-containing olefinic monomer is N-(2-amino-2-oxoethyl)-N-vinyl imidazolium chloride.

27. A composition according to claim 18 wherein said nitrogen-containing olefinic monomer is N,N-dimethyl-N-(3-sulfopropyl)-3-(acryloyl amino)-1-propaneammonium inner salt.

28. A composition according to claim 18 wherein said nitrogen-containing olefinic monomer is N-acryloylmorpholine.

29. A composition according to claim 18 wherein said olefinic comonomer is selected from the group consisting of acrylamide, styrene sulfonic acid, salt of styrene sulfonic acid, N-methylacrylamide, N,N-dimethylacrylamide, acrylic acid, salt of acrylic acid, N-vinylpyrrolidone, methyl acrylate, methacrylate, vinylic sulfonic acid, salt of vinylic sulfonic acid, 2-acrylamido-2-methylpropanesulfonic acid, salt 2-acrylamido-2-methylpropanesulfonic acid, and combinations of any two or more thereof.

30. A composition according to claim 29 wherein said olefinic comonomer is acrylamide.

31. A composition comprising a clay, a water-soluble polymer, and a liquid wherein said polymer comprises repeat units derived from at least one nitrogen-containing olefinic monomer and at least one olefinic comonomer;

said nitrogen-containing olefinic monomer has a formula selected from the group consisting of N-acryloyl morpholine, N-acryloyl-N'-methyl piperazine, N-acryloyl-N'-ethyl piperazine, N-acryloyl-N'-propyl piperazine, N-acryloyl-N'-(3-sulfopropyl)-N'-methyl piperazinium inner salt, N-acryloyl-N'-(3-sulfopropyl)-N'-ethyl piperazinium inner salt, N-acryloyl-N'-(4-sulfopropyl)-N'-methyl piperazinium inner salt, N-acryloyl-N'-(4-sulfopropyl)-N'-ethyl piperazinium inner salt, N-acryloyl-N'-(2-amino-2-oxoethyl)-N'-methyl piperazinium chloride, N-acryloyl-N'-(3-amino-3-oxopropyl)-N'-methyl piperazinium chloride, N-acryloyl-N'-(4-amino-4-oxobutyl)-N'-methyl piperazinium chloride, N-acryloyl-N'-(2-amino-2-oxoethyl)-N'-ethyl piperazinium chloride, N-acryloyl-N'-(3-amino-3-oxopropyl)-N'-ethyl piperazinium chloride, N-acryloyl-N'-(4-amino-4-oxobutyl)-N'-ethyl piperazinium chloride, N,N-dimethyl-N-(3-sulfopropyl)-N-(4-vinylbenzyl) ammonium inner salt, N,N-dimethyl-N-(4-sulfobutyl)-N-(4-vinylbenzyl) ammonium inner salt, N,N-diethyl-N-(3-sulfopropyl)-N-(4-vinylbenzyl) ammonium inner salt, N,N-diethyl-N-(4-sulfobutyl)-N-(4-vinylbenzyl) ammonium inner salt, N,N-dimethyl-N-(3-sulfopropyl)-N-(3-vinylbenzyl) ammonium inner salt, N,N-dimethyl-N-(4-sulfobutyl)-N-(3-vinylbenzyl) ammonium inner salt, N,N-diethyl-N-(3-sulfopropyl)-N-(3-vinylbenzyl) ammonium inner salt, N,N-diethyl-N-(4-sulfobutyl)-N-(3-vinylbenzyl) ammonium inner salt, N,N-dimethyl-N-(2-amino-2-oxoethyl)-N-(4-vinylbenzyl) ammonium chloride, N,N-diethyl-N-(2-amino-2-oxoethyl)-N-(4-vinylbenzyl) ammonium chloride, N,N-dimethyl-N-(3-amino-3-oxopropyl)-N-(4-vinylbenzyl) ammonium chloride, N,N-diethyl-N-(3-amino-3-oxopropyl)-N-(4-vinylbenzyl) ammonium chloride, N,N-dimethyl-N-(2-amino-2-oxoethyl)-N-(3-vinylbenzyl) ammonium chloride, N,N-diethyl-N-(2-amino-2-oxoethyl)-N-(3-vinylbenzyl) ammonium chloride, N,N-dimethyl-N-(3-amino-3-oxopropyl)-N-(3-vinylbenzyl) ammonium chloride, N,N-diethyl-N-(3-amino-3-oxopropyl)-N-(3-vinylbenzyl) ammonium chloride, N-(2-amino-2-oxoethyl)-N'-vinyl imidazolium chloride, N-(3-amino-3-oxopropyl)-N'-vinyl imidazolium chloride, N-(4-amino-4-oxobutyl)-N'-vinyl imidazolium chloride, N,N-dimethyl-N-(3-sulfopropyl)-3-(acryloyl amino)-1-propaneammonium inner salt, N,N-diethyl-N-(3-sulfopropyl)-3-(acryloyl amino)-1-propaneammonium inner salt, N,N-dimethyl-N-(4-sulfobutyl)-3-(acryloyl amino)-1-propaneammonium inner salt, N,N-diethyl-N-(4-sulfobutyl)-3-(acryloyl amino)-1-propaneammonium inner salt, N,N-dimethyl-N-(3-sulfopropyl)-2-(acryloyl amino)-1-ethaneammonium inner salt, N,N-diethyl-N-(3-sulfopropyl)-2-(acryloyl amino)-1-ethaneammonium inner salt, N,N-dimethyl-N-(4-sulfobutyl)-2-(acryloyl amino)-1-ethaneammonium inner salt, N,N-diethyl-N-(4-sulfobutyl)-2-(acryloyl amino)-1-ethaneammonium inner salt, and combinations of any two or more thereof; and said olefinic comonomer is selected from the group consisting of acrylamide, styrene sulfonic acid, salt of styrene sulfonic acid, N-methylacrylamide, N,N-dimethylacrylamide, acrylic acid, salt of acrylic acid, N-vinylpyrrolidone, methyl acrylate, methacrylate, vinylic sulfonic acid, salt of vinylic sulfonic acid, 2-acrylamido-2-methylpropanesulfonic acid, salt 2-acrylamido-2-methylpropanesulfonic acid, and combinations of any two or more thereof.

32. A composition according to claim 31 wherein said nitrogen-containing olefinic monomer is N-acryloyl-N'-methyl piperazine.

33. A composition according to claim 31 wherein said nitrogen-containing olefinic monomer is N-acryloyl-N'-(3-sulfopropyl)-N'-methyl piperazinium inner salt.

34. A composition according to claim 31 wherein said nitrogen-containing olefinic monomer is N-acryloyl-N'-(2-amino-2-oxoethyl)-N'-methyl piperazinium chloride.

35. A composition according to claim 31 wherein said nitrogen-containing olefinic monomer is N,N-dimethyl-N-(3-sulfopropyl)-N-(4-vinylbenzyl) ammonium inner salt.

36. A composition according to claim 31 wherein said nitrogen-containing olefinic monomer is N,N-dimethyl-N-(2-amino-2-oxoethyl)-N-(4-vinylbenzyl) ammonium chloride.

37. A composition according to claim 31 wherein said nitrogen-containing olefinic monomer is N-(2-amino-2-oxoethyl)-N'-vinyl imidazolium chloride.

38. A composition according to claim 31 wherein said nitrogen-containing olefinic monomer is N,N-dimethyl-N-(3-sulfopropyl)-3-(acryloyl amino)-1-propaneammonium inner salt.

39. A composition according to claim 31 wherein said nitrogen-containing olefinic monomer is N-acryloylmorpholine.

40. A composition according to claim 31 wherein said olefinic comonomer is acrylamide.

41. A drilling process comprising introducing a composition into a subterranean formation wherein said composition comprises a clay, a polymer, and a liquid;

said polymer comprises repeat units derived from a nitrogen-containing olefinic monomer having the formula selected from the group consisting of

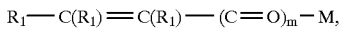
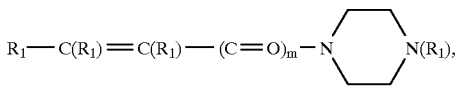
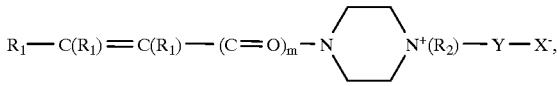
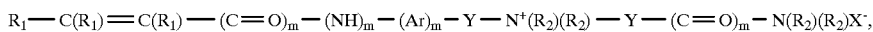
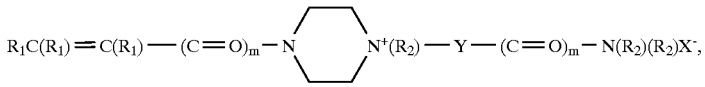
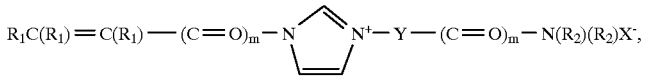

and combinations of any two or more thereof wherein each $R_1$ and $R_2$ are the same or different and independently selected from the group consisting of hydrogen, alkyl radical, aryl radical, aralkyl radical, alkaryl radical, and combinations of any two or more thereof wherein each radical contains 1 to about 30 carbon atoms;

M is a substituted or unsubstituted morpholine group;

X is an anion selected from the group consisting of halide, sulfate, phosphate, nitrate, sulfonate, phosphonates, sulfinate, phosphinate, and combinations of any two or more thereof;

each Y is independently selected from the group consisting of alkylene radical, phenylene group, imidazolium group, naphthylene group, biphenylene group, and combinations of any two or more thereof;

Ar is an arylene group; and each m is independently 0 or 1.

42. A process according to claim 41 wherein said polymer further comprises repeat units derived from at least one olefinic comonomer having the formula selected from the group consisting of $R_1$—C($R_1$)=C($R_1$)—W, $R_1$—C($R_1$)=C($R_1$)-(C=O)$_m$—Z, $R_1$—C($R_1$)=C($R_1$)—Y—W, $R_1$C($R_1$)=C($R_1$)—(C=O)$_m$—N($R_2$)—Y—$R_2$, $R_1$—C($R_1$)=C($R_1$)—(C=O)$_m$—G—Y—Z, $R_1$C($R_1$)=C($R_1$)—(C=O)$_m$—G—Y—W, $R_1$—C($R_1$)=C($R_1$)—(C=O)$_m$—Y—Z, and combinations of any two or more thereof wherein each $R_1$ and $R_2$ are the same or different and are independently selected from the group consisting of hydrogen, alkyl radical, aryl radical, aralkyl radical, alkaryl radical, and combinations of any two or more thereof;

each m is independently 0 or 1;

Z has the formula selected from the group consisting of $N(R_2)(R_2)$, $N^+(R_2)(R_2)(R_2)X^-$;

G is $N(R_2)$ or O;

X is an anion selected from the group consisting of halide, sulfate, phosphate, nitrate, sulfonate, phosphonates, sulfinate, phosphinate, and combinations of any two or more thereof;

each Y is independently selected from the group consisting of alkylene radical, phenylene group, imidazolium group, naphthylene group, biphenylene group, and combinations of two or more thereof; and W is an acid moiety selected from the group consisting of phosphinic acid, phosphonic acid, sulfinic acid, sulfonic acid, sulfuric acid, sulfurous acid, carboxylic acid, phosphoric acid, ammonium salt or alkali metal salt of any of these acids, and combinations of any two or more thereof.

43. A process according to claim 41 wherein said nitrogen-containing olefinic monomer is selected from the group consisting of N,N-dimethyl-N-(3-sulfopropyl)-N-(4-vinylbenzyl) ammonium inner salt, N,N-dimethyl-N-(3-sulfobutyl)-N-(4-vinylbenzyl) ammonium inner salt, N,N-diethyl-N-(3-sulfopropyl)-N-(4-vinylbenzyl) ammonium inner salt, N,N-diethyl-N-(3-sulfobutyl)-N-(4-vinylbenzyl) ammonium inner salt, N,N-dimethyl-N-(3-sulfopropyl)-N-(3-vinylbenzyl) ammonium inner salt, N,N-dimethyl-N-(3-sulfobutyl)-N-(3-vinylbenzyl) ammonium inner salt, N,N-diethyl-N-(3-sulfopropyl)-N-(3-vinylbenzyl) ammonium inner salt, N,N-diethyl-N-(3-sulfobutyl)-N-(3-vinylbenzyl) ammonium inner salt, N-acryloyl-N'-methyl-N'-(2-amino-2-oxoethyl) piperazinium chloride, N-acryloyl-N'-methyl-N'-(3-amino-3-oxopropyl) piperazinium chloride, N-acryloyl-N'-methyl-N'-(4-amino-4-oxobutyl) piperazinium chloride, N-acryloyl-N'-ethyl-N'-(2-amino-2-oxoethyl) piperazinium chloride, N-acryloyl-N'-ethyl-N'-(3-amino-3-oxopropyl) piperazinium chloride, N-acryloyl-N'-ethyl-N'-(4-amino-4-oxobutyl) piperazinium chloride, N,N-dimethyl-N-(2-amino-2-oxoethyl)-N-(4-vinylbenzyl) ammonium chloride, N,N-diethyl-N-(2-amino-2-oxoethyl)-N-(4-vinylbenzyl) ammonium chloride, N,N-dimethyl-N-(3-amino-3-oxopropyl)-N-(4-vinylbenzyl) ammonium chloride, N,N-diethyl-N-(3-amino-3-oxopropyl)-N-(4-vinylbenzyl) ammonium chloride, N-(2-amino-2-oxoethyl)-N'-vinylimidazolium chloride, N-(3-amino-3-oxopropyl)-N'-vinylimidazolium chloride, N-(4-amino-4-oxobutyl)-N'-vinylimidazolium chloride, and combinations of any two or more thereof.

44. A process according to claim 42 wherein said nitrogen-containing olefinic monomer has the formula selected from the group consisting of N,N-dimethyl-N-(3-sulfopropyl)-N-(4-vinylbenzyl) ammonium inner salt, N,N-dimethyl-N-(3-sulfobutyl)-N-(4-vinylbenzyl) inner salt, N,N-diethyl-N-(3-sulfopropyl)-N-(4-vinylbenzyl)

ammonium inner salt, N,N-diethyl-N-(3-sulfobutyl)-N-(4-vinylbenzyl) ammonium inner salt, N,N-dimethyl-N-(3-sulfopropyl)-N-(3-vinylbenzyl) ammonium inner salt, N,N-dimethyl-N-(3-sulfobutyl)-N-(3-vinylbenzyl) ammonium inner salt, N,N-diethyl-N-(3-sulfopropyl)-N-(3-vinylbenzyl) ammonium inner salt, N,N-diethyl-N-(3-sulfobutyl)-N-(3-vinylbenzyl) ammonium inner salt, N-acryloyl-N'-methyl-N'-(2-amino-2-oxoethyl) piperazinium chloride, N-acryloyl-N'-methyl-N'-(3-amino-3-oxopropyl) piperazinium chloride, N-acryloyl-N'-methyl-N'-(4-amino-4-oxobutyl) piperazinium chloride, N-acryloyl-N'-ethyl-N'-(2-amino-2-oxoethyl) piperazinium chloride, N-acryloyl-N'-ethyl-N'-(3-amino-3-oxopropyl) piperazinium chloride, N-acryloyl-N'-ethyl-N'-(4-amino-4-oxobutyl) piperazinium chloride, N,N-dimethyl-N-(2-amino-2-oxoethyl)-N-(4-vinylbenzyl) ammonium chloride, N,N-diethyl-N-(2-amino-2-oxoethyl)-N-(4-vinylbenzyl) ammonium chloride, N,N-dimethyl-N-(3-amino-3-oxopropyl)-N-(4-vinylbenzyl) ammonium chloride, N,N-diethyl-N-(3-amino-3-oxopropyl)-N-(4-vinylbenzyl) ammonium chloride, N-(2-amino-2-oxoethyl)-N'-vinylimidazolium chloride, N-(3-amino-3-oxopropyl)-N'-vinylimidazolium chloride, N-(4-amino-4-oxobutyl)-N'-vinylimidazolium chloride, and combinations of any two or more thereof.

45. A process according to claim 42 wherein said olefinic comonomer is acrylamide.

46. A process according to claim 42 wherein said nitrogen-containing olefinic monomer is N-acryloyl-N'-methyl piperazine.

47. A process according to claim 42 wherein said nitrogen-containing olefinic monomer is N-acryloyl-N'-(3-sulfopropyl)-N'-methyl piperazinium inner salt.

48. A process according to claim 42 wherein said nitrogen-containing olefinic monomer is N-acryloyl-N'-(2-amino-2-oxoethyl)-N'-methyl piperazinium chloride.

49. A process according to claim 42 wherein said nitrogen-containing olefinic monomer is N,N-dimethyl-N-(3-sulfopropyl)-N-(4-vinylbenzyl) ammonium inner salt.

50. A process according to claim 42 wherein said nitrogen-containing olefinic monomer is N,N-dimethyl-N-(2-amino-2-oxoethyl)-N-(4-vinylbenzyl) ammonium chloride.

51. A process according to claim 42 wherein said nitrogen-containing olefinic monomer is N-(2-amino-2-oxoethyl)-N'-vinyl imidazolium chloride.

52. A process according to claim 42 wherein said nitrogen-containing olefinic monomer is N,N-dimethyl-N-(3-sulfopropyl)-3-(acryloyl amino)-1-propaneammonium inner salt.

53. A process according to claim 42 wherein said nitrogen-containing olefinic monomer is N-acryloylmorpholine.

* * * * *

UNITED STATES PATENT AND TRADEMARK OFFICE
CERTIFICATE OF CORRECTION

PATENT NO.    : 5,922,653

DATED         : July 13, 1999

INVENTOR(S)   : Iqbal Ahmed, Ahmad Moradi-Araghi, Bharat B. Patel and Wayne S. Stewart It is certified that error appears in the above-identified patent and that said Letters Patent is hereby corrected as shown below:

Column 36, claim 4, line 45, "3-" should be inserted in front of sulfopropyl.

Signed and Sealed this

Twenty-fifth Day of January, 2000

Attest:

Attesting Officer

*Acting Commissioner of Patents and Trademarks*